(12) United States Patent
Yan et al.

(10) Patent No.: US 12,000,005 B2
(45) Date of Patent: Jun. 4, 2024

(54) **POLYNUCLEOTIDE FOR IDENTIFYING THE SEX OF A *GINKGO BILOBA* PLANT AND USE THEREOF**

(71) Applicants: Agricultural Genomics Institute, Chinese Academy of Agricultural Sciences, Shenzhen (CN); Agricultural Genomics Institute at Shenzhen, Chinese Academy of Agricultural Sciences, Shenzhen (CN)

(72) Inventors: Jianbin Yan, Shenzhen (CN); Qinggang Liao, Shenzhen (CN); Junbo Gou, Shenzhen (CN); Ran Du, Shenzhen (CN); Sanwen Huang, Shenzhen (CN)

(73) Assignees: Agricultural Genomics Institute, Chinese Academy of Agricultural Sciences, Shenzhen (CN); AGRICULTURAL GENOMICS INSTITUTE AT SHENZHEN, CHINESE ACADEMY OF AGRICULTURAL SCIENCES, Shenzhen (CN)

( * ) Notice: Subject to any disclaimer, the term of this patent is extended or adjusted under 35 U.S.C. 154(b) by 0 days.

(21) Appl. No.: 17/619,970

(22) Filed: Dec. 16, 2021

(65) Prior Publication Data
US 2022/0364188 A1 Nov. 17, 2022

Related U.S. Application Data

(63) Continuation-in-part of application No. PCT/CN2020/095856, filed on Jun. 12, 2020.

(30) Foreign Application Priority Data

Jun. 21, 2019 (CN) .......................... 201910542612.6

(51) Int. Cl.
C12Q 1/68 (2018.01)
C12Q 1/6895 (2018.01)
C12Q 1/6844 (2018.01)

(52) U.S. Cl.
CPC ......... *C12Q 1/6895* (2013.01); *C12Q 1/6844* (2013.01); *C12Q 2600/13* (2013.01)

(58) Field of Classification Search
None
See application file for complete search history.

(56) References Cited

FOREIGN PATENT DOCUMENTS

| CN | 103374568 A | 10/2013 |
| CN | 106591322 A | 4/2017 |
| CN | 110195068 A | 9/2019 |
| KR | 20150097403 A | 8/2015 |

OTHER PUBLICATIONS

Brenner et al. Li96f04.q7 Ginkgo microsporophyll (NYGB) Ginkgo biloba cDNA 3' mRNA sequence . Accession No. EX934401, Est Nov. 1, 2007.*
Lowe, T., et al. A computer program for selection of oligonucleotide primers for polymerase chain reactions. Nucleic Acids Research, vol. 18(7), p. 1757-1761, 1990.*
Stratagene Catalog. Gene characterization kits. Stratagene Catalog, p. 39, 1988.*
The State Intellectual Property Office of People's Republic of China, First Office Action, Application No. 201910542612.6, dated Jun. 21, 2019.
The State Intellectual Property Office of People's Republic of China, The Second Office Action, Application No. 201910542612.6, dated Jul. 22, 2020.
International Search Report, International application No. PCT/CN2020/095856, The International search report dated Sep. 23, 2020.
Gene expression and phylogenetic analysis of MADS-box family genes in *Ginkgo biloba*, Dong et al. 994-2020 China Academic Journal Electronic Publishing House, May 15, 2018.
MADS-Box Genes in *Ginkgo biloba* and the Evolution of the Agamous Family, Muriel Jager et al. Mol. Biol. Evol. 20(5):842-854. 2003 Society for Molecular Biology and Evolution, Jan. 13, 2003.
Molecular Analyses of MADS-Box Genes Trace Back to Gymnosperms the Invention of Fleshy Fruits, Alessandro Lovisetto et al., Oct. 4, 2011.
Progress on Sex Determinant Mechanism in Horticultural Plants, Zhao Yujie et al., Acta Horticulturae Sinica, Jun. 27, 2018.
Sex Identification of *Gink go biloba* L. by SCAR Markers and Leaf Morphology, Hang Qian et al., Journal of Southwest University (Natural Science Edition) vol. 38 No. 3 Mar. 3, 2016.
The genomic architecture of the sex-determining region and sex-related metabolic variation in Ginkgo biloba, Qinggang Lia et al., The Plant Journal (2020) 104, 1399-1409, Oct. 4, 2020.
Notification to Grant Patent Right for Invention, Application No. or Publication No. 201910542612.6, dated Jun. 6, 2021.

* cited by examiner

*Primary Examiner* — Suryaprabha Chunduru
(74) *Attorney, Agent, or Firm* — Flener IP & Business Law; Zareefa B. Flener

(57) ABSTRACT

Provided is primers, where the primers specifically bind to a polynucleotide and are used to amplify the polynucleotide; and the polynucleotide comprises or consists of the following sequence: 1) the nucleotide sequence represented by SEQ ID NO: 5; or 2) the complete complementary sequence of the sequence represented by SEQ ID NO: 5; or 3) a nucleotide sequence being identical to 300 bp or more contiguous nucleotides in the sequence of the above 1) or 2), where the nucleotide sequence being identical to 300 bp or more contiguous nucleotides is unique to a male *Ginkgo biloba* plant; and the sequences of the primers are respectively represented by SEQ ID NO: 1 and SEQ ID NO: 2.

1 Claim, 7 Drawing Sheets

Specification includes a Sequence Listing.

```
                      *         20          *         40
reference    : TAGAAAATAT GTG AGATAAAT TTTGTGTTAATGAAA  : 40
Contig1634   : TAGAAAATAT TG  AGATAAAT TTTGTGTTAATGAAT  : 40
               TAGAAAATAT TG  AGATAAAT TTTGTGTTAATGAA

*         60          *         80
reference    : A AAAAAA ATTAATGTACT TTTT TAAAT TATAAAT  : 80
Contig1634   : A AAAAAA-ATTAATGTA   TTTT TAAAT TATAAAT-- : 77
               A AAAAAA ATTAATGTA   TTTT TAAAT TATAAAT

*        100          *        120
reference    : AAAAAAA TTAAATAAGTG -ACCTA TAAAATAAAAT   : 119
Contig1634   : AAAAAAGT TTAAATAAG GTA T  TAAAATAAAAT    : 117
               AAAAAA  TTAAATAAG  G  A   TA TAAAATAAAAT

*        140          *        160
reference    : ATATTTTGT CATAA  TTTTTAAAT TATGTTA AGATC : 159
Contig1634   : GATATTTG  CATAC  TTTTAAAT  TATGTTA AGATC : 157
                ATATTTG  CATAA  TTTTTAAAT TATGTTA AGATC

*        180          *        200
reference    : AAA T TGC AGAATAATTAAT AATGT AAT AAT     : 199
Contig1634   : AATTG GTGCC AGAATAATTAAT GATGT-- AATCT AAT : 195
               AAA T  TGC AGAATAATTAAT  AATGT   AAT  AAT

*        220          *        240
reference    : C TGTCAT TTAAT T TTATAAACAATA AGACAG T   : 239
Contig1634   : CG TGTCAT TTAATC  TTATAAACAATA AGACAGC   : 235
               C  TGTCAT TTAAT   TTATAAACAATA AGACAG T

*        260          *        280
reference    : CAAATAG AC AATTTGATGT TCATAAGAGCCTCTTA A : 279
Contig1634   : CAAATAG AC AATTTGATG  TCATAAGAGCCTCTTA T : 275
               CAAATAG AC AATTTGATG  TCATAAGAGCCTCTTA A

*        300          *        320
reference    : TTAT GTTTGAAAGCAAAT TTGTGCAAAATAAGCACAAAT : 319
Contig1634   :  A  GTTTGAAAGCAAA  TTGTGCAAAATAAGCACAAAT  : 315
                A  GTTTGAAAGCAAAA  TTGTGCAAAATAAGCACAAAT

*        340          *        360
reference    : CACTCAAACAA ATCTTTT T C AAGT TCTTGAACT   : 359
Contig1634   : CACTCAAACAA ATCTTTT --G GAAC TTCTTGAACT   : 353
               CACTCAAACAA ATCTTTT    C G AAG  TTCTTGAACT

*        380          *        400
reference    : TTTGT ACATATCAAAAT GACTG AATTAAATTG ACAT : 399
Contig1634   : TTTGT ACATATCAAAAT ACTGG AATTAAATTGT ACAT : 393
               TTTGT ACATATCAAAAT  ACTG AATTAAATTG  ACAT
```

Fig. 2A

```
                          *         420          *         440
reference  : CTAAAACAGAATCCATTTCACTACTCATATAGTTTCAT :  439
Contig1634 : CTAAAACAAATCCATTTCACTACTCATGAAAGTGTCAT :  433
             CTAAAACA AATCCATTTCACTACTCAT A AGT TCAT

*         460          *         480
reference  : AAACTTGGAGTTTGACAG-AAAATGGGCACAAAAAACC :  478
Contig1634 : AAACTTGGAGTTTGACAGAAAAATGGGCACAACATACC :  473
             AAAC TGGAGTTTGACAG AAAATGGGCACAA A A ACC

*         500          *         520
reference  : AAATAATGAAACAATAACCATTTTCTCTCTTGGAGTCTC :  518
Contig1634 : AAATAATGAAACGATATCCATTTCTCTCTTGGACCTC   :  513
             AAATAATGAAAC ATA CCATT  C TCTCTTGGA CTC

*         540          *         560
reference  : TTTACTTGAGAGTTGAGTTTGAAAATGGGTGCAAA    :  557
Contig1634 : TTGTACCTTGAGAGTTGAGTGTTGAAAAGGGTG------:  548
             TT AC TTGAGAG TGA T TTGAAAA GGGTG

*         580          *         600
reference  : TTTTTTGAGATAAGGATCAAGACAATTTTATTTGTC    :  597
Contig1634 : --------------------CAAGACAATTTTATTTGTC :  567
                                 CAAGACAATTTTATTTGTC

*         620          *         640
reference  : ATGAACAAAAGTTCCACAGAAACAAAATCATTTCATGTT :  637
Contig1634 : ATGAACAAAAGTTCCACAGAAACAAAATCATTTAATGTA :  607
             ATGAACAAAAGTT CACAGAAACAAAATCATTT ATG T

*         660          *         680
reference  : AGAATAGCATCATTAAGTACAAAATGCAAAGCAAAATGGA:  677
Contig1634 : AGAAAAGCATCATTAAGTATAAAATGCAAAGCAAAATGGA:  647
             AGAA AGCATCATTAAGTA AAAATGCAAAGCAAAATGGA

*         700          *         720
reference  : TGAAAAATAAATTTAAATATTTGAGAAATACCTATTTATT :  717
Contig1634 : TGAAAAACAAATTTAAATATTTGAGAAATACCTATTTATT :  687
             TGAAAAA AAATTTAAATATTTGAGAAATACCTATTTATT

*         740          *         760
reference  : GATCCTATGGAAACCATTGGGCACGTTGATACCAATGGTA :  757
Contig1634 : GATCCTACTGAAACCACGGGCACGTTGATACCAATGGTA  :  727
             GATCCTA  GAAACCA  GGGCACGTTGATACCAATGGTA

*         780          *         800
reference  : TCTGTAACCCATTTTATGTTCTAGTGGTAGAAAAAATAT :  797
Contig1634 : TCTCTAACCCATTTTATGTTCTAGTCAAGAAAAAATAT  :  767
             TCT TAACCCATTTTATGTT TAGT  AGAAAAAATAT
```

Fig. 2B

```
                            *          820          *          840
reference   : ATGTATATACAAATTGATATAGCGAACATTATTAAACAA : 837
Contig1634  : ATGTATATACAAATTGATA A  GAAG------------- : 794
              ATGTATATACAAATTGATA A  GAAG

*          860          *          880
reference   : ATTGTTACTAAAATATAGTAAATATCGTATCATTGT : 877
Contig1634  : ----------------------AT G TATCAT GT : 808
                                    AT G TATCAT GT

*          900          *          920
reference   : TGGCATGAAAATGATGAATTATTGATACTCAATGCACAA : 917
Contig1634  : TGGCATGAAAATG TGG TTATT TACTCAATGCACAA : 848
              TGG ATGAAAATG TG A TTATT ATACTCAATGCACAA

*          940          *          960
reference   : ATGAGAACCTTACCTGCTACCTGCGCTTGAGTACTCAAAA : 957
Contig1634  : ATGAGAACCTTACCTGCTACCTG GCTTGAGTACTCAAAA : 888
              ATGAGAACCTTACCTGCTACCTG GCTTGAGTACTCAAAA

*          980          *          1000
reference   : GTTTTCCTGTGCTAGAGAAAATGATGAGTGCAACTTCAG : 997
Contig1634  : TGTTTTCCTGTGCTAGAGAAAATGATGAGTGCAACTTCAG : 928
               GTTTTCCTGTGCTAGAGAAAATGATGAGTGCAACTTCAG

*          1020         *          1040
reference   : CAGCGCATAATATTGAAAGTTCTGAGCCTTCTTAGAAG : 1037
Contig1634  : CAGCGCATAATATTGAAAGTTC TGAGCCTTCTT AGAAG : 969
              CAGCGCATAATATTGAAAGTTC TGAGCCTTCTT AGAAG

*          1060         *          1080
reference   : CCCTCCTC GCGCTTGGAAAAGGTGACTTGCCTATTGGTG : 1077
Contig1634  : CCCTCCTCTGCGCTTGGAAAAGGTGACTTGCCTAT TGTG : 1008
              CCCTCCTC GCGCTTGGAAAAGGTGACTTGCCTA T GTG

*          1100         *          1120
reference   : GCATTTTCAATCCT TTTATCTCAATCTTACCTCTTCCCA : 1117
Contig1634  : TCATTTTCAATCCT TTTATCTCAATCTTACCTCTTCCCA : 1048
               CATTTTCAATCCT TTTATCTCAATCTTACCTCTTCCCA

*          1140         *          1160
reference   : TTTTATCTATAACACTCCTGGCGGATTAAGAAATGCTT : 1157
Contig1634  : TTTTATCTATAACACTCCGG GGAT ACAGAAATGCTT : 1088
              TTTTATCTATAACA CTCC GG GGAT A AGAAATG TT

*          1180         *          1200
reference   : CTTTGTAATCAGATTGATACACAGTGAGATATGAATATA : 1197
Contig1634  : CTTTGTAATCAGATTGATA ACAGTGAGATATGAA ATA : 1128
              CTTTGTAATCAGATTGATA ACAGTGAGATATGAA ATA
```

Fig. 2C

```
                            *         1220        *         1240
reference  : T ACAAAACACAACTGAAATGCTCAAC AAGA GAG AG : 1237
Contig1634 : A ACAAAACACAACTGAAATGCTCAAC AAGA GAG AG : 1168
             A ACAAAACACAACTGAAATGCTCAAC AAGA GAG AG

*         1260        *         1280
reference  : A AGAGATGATGAA CAGATC GAGAGAAGTCTTAATGAA : 1277
Contig1634 : A AGAGATGATGAA CAGATC GAGAGAAGTCTTAATGAA : 1208
             A AGAGATGATGAA CAGATC GAGAGAAGTCTTAATGAA

*         1300        *         1320
reference  : GACT AGGG TTGTACAAAGTTGTTCCACTG AGGAAAGT : 1317
Contig1634 : GACT AGGG TTGTACAAAGTTGTTCCACTG AGGAAAGT : 1248
             GACT AGGG TTGTACAAAGTTGTTCCACTG AGGAAAGT

*         1340        *         1360
reference  : C TTGAAAAG TGAAATTTCCC AAATGTTAAATATTTT : 1357
Contig1634 : C TTGAAAAG TGAAATTTCCC AAATGTTAAATATTTT : 1288
             C TTGAAAAG TGAAATTTCCC AAATGTTAAATATTTT

*         1380        *         1400
reference  : AATTA TTGTGGA CCTCAAA TTGCACTAATAAAAAGC : 1397
Contig1634 : AATTA TTGTGGA CCTCAAA TTGCACTAATAAAAAGC : 1328
             AATTA TTGTGGA CCTCAAA TTGCACTAATAAAAAGC

*         1420        *         1440
reference  :  CCACTTG CCTAAGGGAGGGGA CCCA TGTGTTGGAC : 1437
Contig1634 : G CCACTTG CCTAAGGGAGGGGA CCCA TGTGTTGGAC : 1368
               CCACTTG CCTAAGGGAGGGGA CCCA TGTGTTGGAC

*         1460        *         1480
reference  : CACTTGTCTAATGGAGT TTAAGTACAGAG T GAGATAG : 1477
Contig1634 : CACTTGTCTAATGGAGT TTAAGTACAGAG T GAGATAG : 1408
             CACTTGTCTAATGGAGT TTAAGTACAGAG T GAGATAG

*         1500        *         1520
reference  : AGCCTG CCAGTTGTTGGGTTTGCCATTTCAGTCAAAAT : 1517
Contig1634 : AGCCTG CCAGTTGTTGGGTTTGCCATTTCAGTCAAAAT : 1448
             AGCCTG CCAGTTGTTGGGTTTGCCATTTCAGTCAAAAT

*         1540        *         1560
reference  : GGACAGAGTTTG AAG ACAC TTGAT T TAGATCAAT : 1557
Contig1634 : GGACAGAGTTTG AAG ACAC TTGAT T TAGATCAAT : 1486
             GGACAGAGTTTG AAG ACAC TTGAT T TAGATCAAT

*         1580        *         1600
reference  : AA AATGGTAAT CT CCACTATCAAATC GATT TCTAA : 1597
Contig1634 : AA AATGGTAAT CT CCACTATCAAATC GATT TCTAA : 1526
             AA AATGGTAAT CT CCACTATCAAATC GATT TCTAA
```

Fig. 2D

```
                         *         1620         *         1640
reference  : ACT GT CGAAAGCTCAGCCAAACA ACTGTATTATT     : 1637
Contig1634 : ACT GT GCGAAAGCTCAGCCAAACA---------------    : 1551
             ACT GT CGAAAGCTCAGCCAAACA

*         1660         *         1680
reference  :    T AA CTCA CCC AATTA AAA T TCA ACTCTCAA  : 1677
Contig1634 : ---T AA TTCA CCC AATTA AAA  TCA ACTCTCAA   : 1588
                T AA CTCA CCC AATTA AAA   TCA ACTCTCAA

*         1700         *         1720
reference  : ATCTTA TTCATCT CAA AAATC CCATCTT A TT  CG  : 1717
Contig1634 : ATCT A TTCATCT  AA AAATC CCATCTT --- TT CG  : 1625
             ATCTTA TTCATCT  AA AAATC CCATCTT     TT GC

*         1740         *         1760
reference  : A ATAATGGT GCCATCTT TTGGA GAAAAT GAATTAT   : 1757
Contig1634 : A TATAATGGT GCCATCTT TTGGA GAAAAT GGAATTAT  : 1665
             A ATAATGGT GCCATCTT TTGGA GAAAAT GAATTAT

*         1780         *         1800
reference  : TCTC AAATCTTTTAAATTCTT  TTTAGTTTTA TCAGG   : 1797
Contig1634 : TCTC AAATCTTTTAAATTCTT CTTTAGTTTTA TCAGG   : 1705
             TCTC AAATCTTTTAAATTCTT  TTTAGTTTTA TCAGG

*         1820         *         1840
reference  : ATTCCTTTA A AAGT AA ATTTT AAATCTATT        : 1837
Contig1634 : ATTCCTTTA----AA TAA---------------           : 1721
             ATTCCTTTA    AA  AA

*         1860         *         1880
reference  : AGTTTTAATCACGATTCTTTACAGGGAGTCTTC CTT      : 1877
Contig1634 : --------------------TA AGGGA TCTTC CTT-     : 1739
                                 TA AGGGA TCTTC CTT

*         1900         *         1920
reference  : AAG AACA TGG ACTGCGTTCATA T GCCTGCT AACCA  : 1917
Contig1634 : AAGTAACA TG TACTGCGTTCATAC GCCTGC  AACCA   : 1779
             AAG AACA TG  ACTGCGTTCATA  GCCTGC  AACCA

*         1940         *         1960
reference  : T GCGGGAT GAC A GAGAGCG T AGTTTGTATGT CCC  : 1957
Contig1634 :   GCGGGAT GAC AT GAGAGCG  AGTTTGTATGT  A   : 1819
             T GCGGGAT GAC A GAGAGCG  AGTTTGTATGT   C

*         1980         *         2000
reference  : AAC AGAGTTATATCGTAAACTTGTGT CTT TAAAGA AG  : 1997
Contig1634 : AAG AGAGTTATATCGTAAACTTGTGT CT  TAAAGA TAG : 1859
             AAC AGAGTTATATCGTAAACTTGTGT CT  TAAAGA AG
```

Fig. 2E

```
                    *         2020        *         2040
reference  : ATACTTAAGAT TAAAAGAA TCAAATATA A TAGTTTTT : 2037
Contig1634 : ATACTTAA AT TAAAAGAA TCAAATATA CC TAGTTTT  : 1899
             ATACTTAA AT TAAAAGAA TCAAATATA    TAGTTTT

*         2060        *         2080
reference  : CTCTAC TAACCCA TTGGAATTTTAACCGAATTCTATGG : 2077
Contig1634 : CTCTAC TAACCCA TTGGAATTTTAACCGAATTCTAT G  : 1939
             CTCTAC TAACCCA TTGGAATTTTAACCGAATTCTAT G

*         2100        *         2120
reference  : ATTTAGCGGTGGC G TTT T T GGGA C ATTT  TAT : 2117
Contig1634 : ATTTAGCGGTGGC   TTT   T GGGA   ATTT  TAT : 1979
             ATTTAGCGGTGGC G TTT T T GGGA C ATTT  TAT

*         2140        *         2160
reference  : TTT AG A CT CA A CCTTT G ATAATGTT TAT  : 2157
Contig1634 : TTT AG A  CT CA  A CCTTT  ATAATGTT TAT G : 2019
             TTT AG A   CT CA  A CCTTT G ATAATGTT TAT

*         2180
reference  : TTTGTA ATAGTAT TCTCA : 2180
Contig1634 : T TT  CTATA A AT TCTCA : 2042
             T TT   A  ATA A AT TCTCA
```

Fig. 2F

SEQUENCE LISTING

```
<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Specific primer-Forward

<400> SEQUENCE: 1
tataattggg gatgagcttt a                                                   21
```

<210> SEQ ID NO 2
<211> LENGTH: 18
<212> TYPE: DNA
<213> ORGANISM: Artificial Sequence
<220> FEATURE:
<223> OTHER INFORMATION: Specific primer-Reverse

<400> SEQUENCE: 2
ggggtgcaag acaatttt                                                   18

<210> SEQ ID NO 3
<211> LENGTH: 19
<212> TYPE: DNA
<213> ORGANISM: Artificial Sequence
<220> FEATURE:
<223> OTHER INFORMATION: Consensus primer-Forward

<400> SEQUENCE: 3
aagagtgtag gtggacacc                                                  19

<210> SEQ ID NO 4
<211> LENGTH: 26
<212> TYPE: DNA
<213> ORGANISM: Artificial Sequence
<220> FEATURE:
<223> OTHER INFORMATION: Consensus primer-Reverse

<400> SEQUENCE: 4
tctcattgtc tgagattcta gcaatc                                          26

<210> SEQ ID NO 5
<211> LENGTH: 2042
<212> TYPE: DNA
<213> ORGANISM: Artificial Sequence
<220> FEATURE:
<223> OTHER INFORMATION: Contig1634

<400> SEQUENCE: 5
tagaaaaata tatgcagata aatgtttgtg ttaatgaaat agaaaaaaat taatgtaaat      60
tttctaaatt tataaataaa aaagtttaa aataagcgta aaatagtaaa ataaaatgat     120
attttggcat aacatttta aatatatgtt aaagatcaaa ttgagtgcca gaataattaa     180
tgaatgtaat ctaatcgctg tcatgtttaa tccttataaa acaataaaga cagctcaaat     240
agaacaaatt tgatgctcat aagagcctct tagataaaag tttgaaagca aaaattgtgc     300
aaaataagca caaatcactc aaacaagatc ttttggcgga agcttcttga acttttgtaa     360
catatcaaaa tcactggaat taaattgtta catgctaaaa caaaatccat ttcactactc     420
atgaaagtgt cataaacttg gagtttgaca gcaaaatggg cacaacatat accaaataat     480
gaaacgatat ccattcccct ctcttggaac ctcttgtact ttgagagtat gactgttgaa     540 aagggggtgca agacaatttt atttgtcatg aacaaaagtt tcacagaaac aaaatcattt     600
aatgttcaga acagcatcat taagtataaa atgcaaagca aaatggatga aaaagaaatt     660
taaatatttg agaaatacct atttattgat cctaatgaaa ccaccgggca cgttgatacc     720
aatggtatct ctaacccatt tttatgttct agtcaaagaa aaaatatatg tatatacaaa     780
ttgatacaca gaagatagtt atcatagttg gcatgaaaat gctggagtta tttatactca     840
atgcacaaat gagaacctta cctgctacct gagcttgagt actcaaaatg ttttcctgtg     900
ctagagaaaa tgatgagtgc aacttcagca gcgcataata ttgaaagttc atgagccttc     960
ttgagaagcc ctcctctgcg cttggaaaag gtgacttgcc tactagtgac attttcaatc    1020

```
cttttatct caatcttacc tcttcccatt ttatctataa cacctccggg cggatcagag    1080
aaatgattct ttgtgaatca gattgataaa cagtgagata tgaaaataga tacaaaacac    1140
aactgaaatg ctcaacaaag acgagtagag agagatgatg aaacagatca gagagaagtc    1200
ttaatgaaga ctgaggggtt gtacaaagtt gttccactgc aggaaagtcc ttgaaaagaa    1260
tgaaatttcc cgaaatgtta aatattttaa ttaattgtgg accctcaaat ttgcactaat    1320
aaaaaagcgc cacttggcct aagggagggg accccaatg tgttggacca cttgtctaat    1380
ggagtcttaa gtacagagtt cgagatagag cctgtccagt tgttgggttt tgccatttca    1440
gtcaaaatgg acagagtttg aagcacactt gatattctag atcaataaaa atggtaattc    1500
tgccactatc aaatcggatt gtctaaactt gtgcgaaagc tcagccaaac ataaagctca    1560
tccccaatta taaagctcat actctcaaat cttagttcat ctaaataaat caccatcttt    1620
ttgccatata atggtagcca tcttcttgga agaaaatgga attattctct aaatctttta    1680
aattcttcgt ttagttttac tcaggattcc tttaaaacta ataaagggaa tcttctctta    1740
agtaacaatg atactgcgtt catacaggcc tgcaaaccat agcgggatgg acaatgagag    1800
cgcaagtttg tatgtaaaca acgagagtta tatcgtaaac ttgtgtccta taaagataga    1860
tacttaacat gtaaaagaac tcaaatatac ctagttttcc tctacgtaac ccatttggaa    1920
ttttaaccga attctataga tttagcggtg gctgctttct atagggaact attttatatt    1980
tttaggaccc ttcacgatcc tttcgtataa tgttgtatgt cttaaactat aaaaatatct    2040
ca                                                                   2042

<210> SEQ ID NO 6
<211> LENGTH: 369
<212> TYPE: DNA
<213> ORGANISM: Artificial Sequence
<220> FEATURE:
<223> OTHER INFORMATION: Contig1634 encoding sequence

<400> SEQUENCE: 6
atgtcactag taggcaagtc accttttcca agcgcagagg agggcttctc aagaaggctc     60
atgaactttc aatattatgc gctgctgaag ttgcactcat cattttctct agcacaggaa    120
aacattttga gtactcaagc tcaggtagca gtcatactct caaagtacaa gaggttccaa    180 gagagggaa tggatatcgt ttcattattt ggtatatgtt gtgccatttt tgctgtcaaa    240
ctccaagttt atgacacttt catgagtagt gaaatggatt ttgttttagc atgtaacaat    300
ttaattccag tgattttgat atgttacaaa agttcaagaa gcttccgcca aaagatcttg    360
tttgagtga                                                           369

<210> SEQ ID NO 7
<211> LENGTH: 2180
<212> TYPE: DNA
<213> ORGANISM: Unknown
<220> FEATURE:
<223> OTHER INFORMATION: reference genome sequence

<400> SEQUENCE: 7
tagaaaaata tgtggagata aatatttgtg ttaatgaaaa aaaaaaaata ttaatgtact     60 tttttttaaat ctataaatta aaaaaaaaat taaataagt gcacctatta aaataaaata    120
atattttgtc ataaattttt taatttatg ttagagatca aatatatgc aagaataatt    180 aatcaatgta caataaaatc attgtcatat ttaatatttta taaaacaata tagacagatc    240
```

```
aaatagtact aatttgatgt tcataagagc ctcttaaact tatgtttgaa agcaaaattt    300
gtgcaaaata agcacaaatc actcaaacaa catcttttt catgaaagtt tcttgaactt     360
ttgttacata tcaaaatgac tgcaattaaa ttgcaacata ctaaaacaga atccatttca    420
ctactcatca tagtctcata aacatggagt tgacagaaa atgggcacaa aacagaccaa     480
ataatgaaac aatacccatt ttcttctctt ggagtctctt acacttgaga gattgagtat    540
tgaaaatggg tgtgaaattt tttttcgaga taaggataca agacaattt atttgtcatg     600 aacaaaagtt ccacagaaac aaaatcattt catggttaga atagcatcat taagtacaaa    660
atgcaaagca aaatggatga aaataaatt taaatatttg agaaatacct atttattgat     720
cctatcgaaa ccattgggca cgttgatacc aatggtatct gtaacccatt tttatgttat    780
agtggtagaa aaaatatatg tatatacaaa ttgatatagc gaagattatt gaagaaaat    840 tgttagctaa gaatagagga aatatggcta tcattgttgg aatgaaaatg atgaaattat    900
taatactcaa tgcacaaatg agaaccttac ctgctacctg cgcttgagta ctcaaaaagt    960
tttcctgtgc tagagaaaat gatgagtgca acttcagcag cgcataatat tgaaagttcg   1020
tgagccttct tcagaagccc tcctcggcgc ttggaaaagg tgacttgcct attggtggca   1080
ttttcaatcc tctttatctc aatcttacct cttcccattt tatctataac aactcctgga   1140
ggattacaga aatgtttctt tgtgaatcag attgatagac agtgagatat gaatatataa   1200
acaaaacaca actgaaatgc tcaacgaaga ggaggagaaa gagatgatga accagatctg   1260
agagaagtct taatgaagac ttagggattg tacaaagttg ttccactgta ggaaagtact   1320
tgaaaaagct gaaatttccc caaatgttaa atattttaat tatttgtgga tcctcaaact   1380
tgcactaata aaaagcacc acttgtccta agggaggggg agcccagtgt gttggaccac     1440
ttgtctaatg gagtattaag tacagagctt gagatagagc ctgcccagtt gttgggtttt   1500
gccatttcag tcaaaatgga cagagtttga aagtacacat tgatggtata gatcaataac   1560
aatggtaatg cttccactat caaatcagat tctctaaact cgtacgaaag ctcagccaaa   1620
cagcctgtga atcagtcttc ttaatctcaa ccctaattaa aaatttcaca ctctcaaatc   1680
ttacttcatc tcaacaaatc cccatcttta attagcgaga taatggttgc catctttttg   1740
gaggaaaata gaattattct caaaatcttt taaattctta ctttagttt aatcaggatt     1800 cctttacagg aagtcaaaat cttttaaatt cttactttag ttttaatcag gattccttta   1860
cagggagtct tcccttcaag caacattggc actgcgttca taatagcctg ctaaccatgg   1920
cgggatagac tacgagagcg tgagtttgta tgtccccaac aagagttata tcgtaaactt   1980 gtgttctta agagagata cttaagatat aaaagaattc aaatataaat agttttctc      2040 tacctaaccc aattggaatt ttaaccgaat tctatggatt tagcggtggc cgttttatgt   2100
ggggagcaat tttgtatttt aagaaagctc cattagcctt ttgcataatg ttttatattt   2160
tgtaacatag atatgtctca                                                2180
```

POLYNUCLEOTIDE FOR IDENTIFYING THE SEX OF A *GINKGO BILOBA* PLANT AND USE THEREOF

CROSS-REFERENCE TO RELATED APPLICATIONS

This application is a continuation-in-part of International Application No. PCT/CN2020/095856, filed on Jun. 12, 2020, which claims priority to Chinese Patent Application No. 201910542612.6, filed on Jun. 21, 2019. The disclosures of the aforementioned applications are hereby incorporated by reference in their entireties.

TECHNICAL FIELD

This application relates to the field of identification the sex of a *Ginkgo biloba* plant, in particular to a polynucleotide for identifying the sex of a *Ginkgo biloba* plant and use thereof.

BACKGROUND ART

*Ginkgo* (*Ginkgo biloba* L.) integrates medicinal, edible, material and ornamental use, and has special economic value and important scientific research value. In recent years, the *ginkgo* industry in China has developed rapidly, and its planting scale has gradually expanded. *Ginkgo* is especially widely used in landscaping projects. *Ginkgo* is a dioecious plant, and it takes 15-20 years from planting seedlings to blooming and bearing fruit, then a male plant can be distinguished from a female plant. However, the *ginkgo* seeds have a special smell during the mature period, in the city streets when their seeds drop and rot, the street will be polluted. Therefore, as an urban greening tree species, only male plants are needed instead of female plants for the purpose of producing *ginkgo*. Researchers at home and abroad have conducted research on its morphology, physiological and biochemical indicators, isozyme spectrum, chemical treatment and chromosome karyotype, however there are problems for identifying the sex of plant by using the above methods, such as complicated operation, high cost, and low reliability.

Identifying plant gender by morphological characteristics is relatively simple and intuitive; it only needs to observe and compare the morphological characteristics of plants, and the operation is relatively simple. Although the methods of observing tree shapes and leaf splits are simple and easy to implement, judging with these indicators will be significantly affected by subjective factors, the lack of clear standards for digitization, diagram and spectrum makes it easy to make mistakes. Although the judgment of organs is both accurate and simple, it may only be observed after passing the juvenile period of a plant, accordingly early identification is difficult. Studies have shown that there are differences between male and female *Ginkgo biloba* in physiological and biochemical indicators, but such differences will be affected by multiple factors including climate, growing environment, tree age, etc. Physiological and biochemical indicators mostly seek to measure certain differences between the adult male and female plants in different aspects, but whether they may be used for early gender identification of seedlings needs further research. At present, chromosome morphology is one of the important methods for gender identification of *Ginkgo biloba*, and it is also the most direct genetic evidence. However, there is no conclusion on whether the gender determination mechanism of *Ginkgo biloba* is XY or ZW according to karyotype observations, thus it is of no practical significance for judging the gender of a plant by karyotype observations.

CONTENTS OF THE INVENTION

In view of this, this application provides a polynucleotide for early identification of the sex of a *Ginkgo biloba* plant. The operation is simple, and the accuracy is high.

For purpose of this application, the following technical solutions are adopted:

In one aspect of this application, provided is a polynucleotide for identifying the sex of a *Ginkgo biloba* plant, wherein it includes or consists of the following sequence:
1) the nucleotide sequence represented by SEQ ID NO: 5; or
2) a complementary sequence, degenerate sequence, or homologous sequence of the sequence represented by SEQ ID NO: 5, wherein the homologous sequence is a polynucleotide having about 30% or more, about 40% or more, about 50% or more, about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more identity with the polynucleotide represented by SEQ ID NO: 5, or the corresponding cDNA molecule thereof; or
3) a polynucleotide hybridizing to the nucleotide sequence represented by SEQ ID NO: 5 under stringent conditions or a complementary sequence thereof; or
4) the coding sequence of any one of the sequences of the above 1)-3); or
5) a nucleotide sequence being identical to more than 10 bp contiguous nucleotides in any one of the sequences of the above 1)-4), wherein this sequence is unique to a male *Ginkgo biloba* plant, and at least one base in the nucleotide sequence being identical to said more than 10 bp contiguous nucleotides is unique to a male *Ginkgo biloba* plant.

In a particular embodiment of the application, the coding sequence is represented by SEQ ID NO: 6.

In a particular embodiment of the application, the nucleotide sequence of the above 5) is a nucleotide sequence being identical to the contiguous nucleotides in any one of the sequences of the above 1)-4) with any one of the number of nucleotides between 10-2042 bp, e.g., 10, 11, 12, 13, 14, 15, 16, 18, 20, 22, 25, 28, 30, 40, 50, 60, 70, 80, 90, 100, 120, 150, 200, 300, 400, 500, 800, 1000, 1200, 1550, 1701, 1832, 1908, 2042, etc.

In a particular embodiment of the application, the number of bases unique to a male *Ginkgo biloba* plant is 1, 2, 3, 4, 5, 6, or more.

In another aspect of the application, provided is a biological material associated with the above polynucleotide, which is selected from:
A1): a protein encoded by the polynucleotide;
A2): an expression cassette including the polynucleotide;
A3): a recombinant vector including the polynucleotide;

A4): a recombinant vector including the expression cassette of A2);

A5): a recombinant microorganism including the polynucleotide;

A6): a recombinant microorganism including the expression cassette of A2);

A7): a recombinant microorganism including the recombinant vector of A3);

A8): a recombinant microorganism including the recombinant vector of A4);

A9): a plant cell line including the polynucleotide;

A10): a plant cell line including the expression cassette of A2);

A11): a plant cell line including the recombinant vector of A3);

A12): a plant cell line including the recombinant vector of A4);

A13): a plant grown from the plant cell line of A9)-A12).

In another aspect of the application, provides is an isolated protein molecule, characterized in that the protein molecule is selected from:

1) a protein encoded or expressed by the above polynucleotide;
2) a fusion protein obtained by connecting the N-terminal and/or C-terminal of the protein of the above 1) with a tag;
3) a protein with the same function obtained by substitution, and/or deletion, and/or addition of one or more amino acid residues in the amino acid sequence of the protein of the above 1) or 2);
4) a protein with the same function as, and having 75% or more homology with the amino acid sequence of the protein of any one of the above 1)-3);

wherein the 75% or more homology is 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more.

In another aspect of the application, provided is a plant, which includes the above polynucleotide, and/or the above biological material, and/or the above protein molecule.

In another aspect of the application, provided are primers, which are used to amplify the above polynucleotide, or used to amplify consecutive 30 bp nucleotides in the above polynucleotide.

In a particular embodiment of the application, the primers specifically bind to the above polynucleotide, or specifically bind to consecutive 30 bp nucleotides in the above polynucleotide.

In a particular embodiment of the application, the sequences of the primers are represented by SEQ ID NO: 1 or SEQ ID NO: 2.

In another aspect of the application, provided is a primer pair, which is used for detecting or amplifying the above polynucleotide, or for detecting or amplifying consecutive 30 bp nucleotides in the above polynucleotide.

In a particular embodiment of the application, the primer pair includes the primers having the sequences respectively represented by SEQ ID NO: 1 and/or SEQ ID NO: 2.

In a particular embodiment of the application, the primer pair includes a primer pair consisting of the primers having the sequences respectively represented by SEQ ID NO: 1 and SEQ ID NO: 2.

In a particular embodiment of the application, the primer pair further includes the primers having the sequences respectively represented by SEQ ID NO: 3 and/or SEQ ID NO: 4.

In a particular embodiment of the application, the primer pair further includes a primer pair consisting of the primers having the sequences respectively represented by SEQ ID NO: 3 and SEQ ID NO: 4.

In a particular embodiment of the application, the primer pair includes a primer pair with the sequences respectively represented by SEQ ID NO: 1 and SEQ ID NO: 2, and a primer pair with the sequences respectively represented by SEQ ID NO: 3 and SEQ ID NO: 4.

In another aspect of the application, provided is a kit for identifying the sex of a *Ginkgo biloba* plant, wherein the kit includes the above primers or primer pair.

In a particular embodiment of the application, the kit includes specific primers represented by SEQ ID NO: 1 and SEQ ID NO: 2.

In a particular embodiment of the application, the kit further includes the consensus primers represented by SEQ ID NO: 3 and SEQ ID NO: 4.

In another aspect of the application, also provided is use of the above polynucleotide, and/or the above biological material or substance, and/or the above protein molecule, and/or the above primers, and/or the above primer pair in the preparation of a kit for identifying the sex of a *Ginkgo biloba* plant.

In another aspect of the application, also provided is a method for identifying the sex of a *Ginkgo biloba* plant, which includes the following steps: amplifying the total DNA of a *Ginkgo biloba* plant which is to be identified by using primers.

In a particular embodiment of the application, the primers include sequences respectively represented by SEQ ID NO: 1 and/or SEQ ID NO: 2.

In a particular embodiment of the application, the primers further include sequences respectively represented by SEQ ID NO: 3 and/or SEQ ID NO: 4.

The primers include specific primers and consensus primers, wherein the specific primers are used to amplify the DNA sequence unique to a male *Ginkgo biloba* plant; and the consensus primers are used to amplify the consensus DNA sequence of a male *Ginkgo biloba* plant and a female *Ginkgo biloba* plant.

In a particular embodiment of the application, the specific primers are primers having the sequences respectively represented by SEQ ID NO: 1 and SEQ ID NO: 2; and the consensus primers are primers having the sequences respectively represented by SEQ ID NO: 3 and SEQ ID NO: 4.

In a particular embodiment of the application, the method for identifying the sex of a *Ginkgo biloba* plant particularly includes the following steps:

1) extracting total DNA of the leaves of a sample for later use, wherein the ratio of A260/A280 is 1.6-2.0;
2) performing PCR amplification on the total DNA of the sample by using the primer pairs.

In a particular embodiment of the application, the specific operations of the method for identifying the sex of a *Ginkgo biloba* plant include:

1) extracting total DNA of the leaves of a sample, wherein the quality of the total DNA is detected by agarose gel electrophoresis and spectrophotometer, so that the integrity of the extracted total DNA is good, and the A260/A280 ratio is 1.6-2.0; then the total DNA is diluted to 100 ng/μL and stored at −20° C. for later use;

2) utilizing the total DNA of the sample as a template to perform PCR amplification by the primer pair, wherein the PCR products are directly detected by 1% agarose gel electrophoresis, and the products of two pairs of primers from the same sample may be spotted in the same lane for detection, taking pictures to record by agarose gel imaging system;

3) analyzing the results: a male sample will have two bands, while a female sample will have only one band; if there is no band, then it indicates that there is a problem with the above DNA template extraction, and samples should be taken again for detection.

Exemplarily, this application has at least one of the following advantages:

The polynucleotide provided herein is unique to a male *Ginkgo biloba* plant. As for identifying the sex of a *Ginkgo biloba* plant by said polynucleotide, it has the advantages of stable and accurate results, good repeatability and fast detection, thereby providing the basis for identifying the sex of a *Ginkgo biloba* plant by molecular markers.

BRIEF DESCRIPTION OF THE DRAWINGS

FIGS. 2A-2F show the alignment results of Contig1634 (SEQ ID NO: 5) provided in the examples of this application and the reference genome sequence (SEQ ID NO: 7 GIGADB (doi:10.5524/100209)). Wherein, FIG. 2A provides the alignment results between bases 1-393 of Contig1634 and bases 1-399 of the reference genome sequence; FIG. 2B provides the alignment results between bases 394-767 of Contig1634 and bases 340-797 of the reference genome sequence; FIG. 2C provides the alignment results between bases 768-1128 of Contig1634 and bases 798-1197 of the reference genome sequence; FIG. 2D provides the alignment results between bases 1129-1526 of Contig1634 and bases 1198-1597 of the reference genome sequence; FIG. 2E provides the alignment results between bases 1527-1859 of Contig1634 and bases 1598-1997 of the reference genome sequence; FIG. 2F provides the alignment results between bases 1860-2042 of Contig1634 and bases 1998-2180 of the reference genome sequence.

DETAILED DESCRIPTION OF EMBODIMENTS

Figure 1:
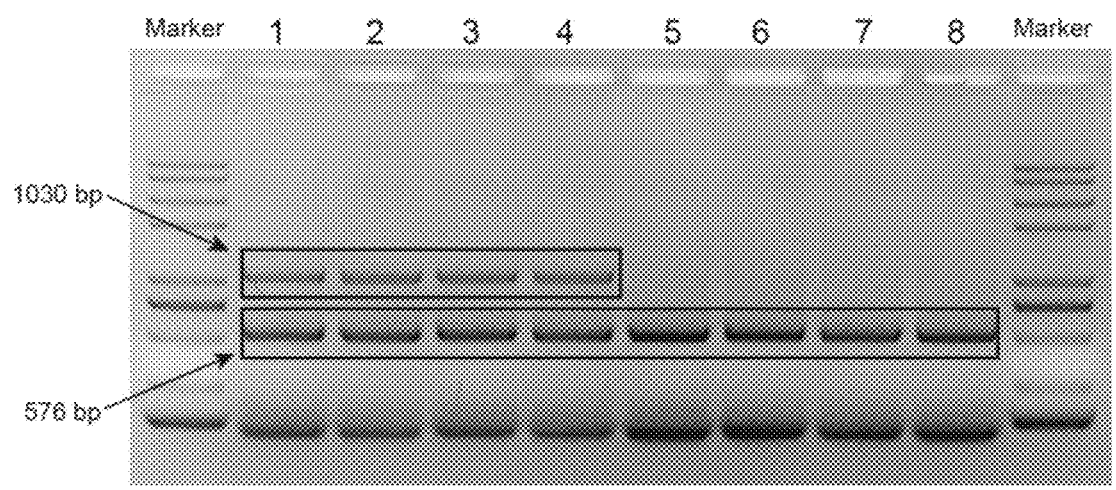
FIG. 1 shows the experimental results of part of the *Ginkgo biloba* plants provided in the examples of the application.

The technical solutions in the examples of the application will be clearly and completely described below in conjunction with the drawings in the examples of the application. Obviously, the described examples are only part of the examples of the application, rather than all the examples. Based on the examples in this application, all other examples obtained by those of ordinary skill in the art without creative work shall fall within the protection scope of this application.

Example 1

1. Synthesis of Primers

The male and female plant populations are re-sequenced, and gender-specific K-mers are obtained by K-mer distribution analysis. On this basis, male-specific sequencing fragments are obtained, and male-specific fragments are obtained through assembly. These fragments are characterized in that: they only exist in male individuals. One fragment of the contigs is selected in this method, and named as Contig1634 (SEQ ID NO: 5) with the specific sequence represented by SEQ ID NO: 5, and the coding sequence is represented by SEQ ID NO: 6. The alignment of Contig1634 with the reference genome sequence (SEQ ID NO: 7 GIGADB (doi:10.5524/100209), from female plants) is shown in FIGS. 2A-2F. It can be seen from FIGS. 2A-2F that there are multiple site differences between Contig1634 and the reference genome, and the different positions are evenly distributed throughout the sequence. The short fragments of Contig1634 may be used to identify this sequence.

The primers designed on the basis of Contig1634 sequence are used as specific primers to amplify the male-specific fragments. The primers designed on the basis of reference genome sequence of *Ginkgo biloba* are used as consensus primers to amplify the fragments shared by male and female plants.

The primer sequences are biosynthesized by Shanghai Sangon Biotech. The purity requirement of the primer synthesis is to be purified by PAGE, and aliquoted into 1 OD/tube. The concentration of the forward and reverse primers is respectively dissolved to 10 μM; particularly, the male-specific primers are: forward primer, SEQ ID NO: 1; reverse primer: SEQ ID NO: 2; and consensus primers of male and female plants are: forward primer, SEQ ID NO: 3; reverse primer: SEQ ID NO: 4. The specific sequences are shown in Table 1 below.

TABLE 1

Primer sequence listing

| SEQ ID | Direction | Primer sequences (5'-3') | Length of the product |
|---|---|---|---|
| NO: 1 | Forward | TATAATTGGGGATGAGCTTTA | 1030 bp |
| NO: 2 | Reverse | GGGGTGCAAGACAATTTT | |
| NO: 3 | Forward | AAGAGTGTAGGTGGACACC | 576 bp |
| NO: 4 | Reverse | TCTCATTGTCTGAGATTCTAGCAATC | |

2. Extraction of Total DNA from Samples of *Ginkgo biloba*

The tender leaves of *Ginkgo biloba* plants that have been identified to be male or female are collected, wherein there are 24 female plants and 23 male plants. The plants are from the *Ginkgo biloba* planting area in Pizhou City, Jiangsu Province (Jiangsu Province, China (34°37'4.98" N; 117°58'14.7" E)). Extracting the total DNA of each plant according to the following steps:

I. taking 0.5 g of tender leaves of each sample *Ginkgo biloba* plant into a 1.5 mL centrifuge tube, then adding liquid nitrogen to grind into powder;

II. adding 600 μL CTAB buffer (2% CTAB, 1.4M NaCl, 0.02M EDTA, 0.1M Tris-HCl, 3% PVP, 2% β-mercaptoethanol) to mix well, staying water bath at 65° C. for 35 min and shaking 2-3 times during this period;

III. after the water bath, taking out the sample and placing it on ice for 10 min, adding an equal volume of phenol/chloroform/isopentanol (25:24:1) to extract for 15 min, then centrifuging at 11000 r·min$^{-1}$ for 10 min at room temperature;

IV. taking the supernatant and adding an equal volume of chloroform/isopentanol (24:1) to extract for 15 min, then centrifuging again at 11000 r·min$^{-1}$ for 10 min;

V. taking the supernatant, and adding 2/3 volume of isopropanol to mix well, then standing at −20° C. for 20 min;

VI. centrifuging at 6000 r·min$^{-1}$ for 5 min, discarding the aqueous solution, then washing the precipitate with 75% alcohol for 2-3 times;

VII. air-drying, and adding 300 μL of TE (PH8.0) including 2 μg RNAase to dissolve;

VIII. after agarose electrophoresis and spectrophotometric detection, adjusting the concentration to 100 ng/μL and storing at −20° C. for later use.

3. Amplification of the Specific Fragment of *Ginkgo biloba* Sample

The amplification reaction is carried out by using EasyTaq® reagents from TransGen Biotech and in accordance with the recommended conditions. A 20 μL reaction system is used, and this PCR system is prepared with the components shown in Table 2 below:

TABLE 2

Amplification reaction system

| Component | Volume | Final concentration |
|---|---|---|
| Template | 2 μL | ~30 ng DNA |
| Forward primer (10 μM) | 0.5 μL | 0.2 μM |
| Reverse primer (10 μM) | 0.5 μL | 0.2 μM |
| 10×EasyTaq ® buffer | 2 μL | 1× |
| 2.5 mM dNTPs | 1.6 μL | 0.2 mM |
| EasyTaq ® DNA polymerase | 0.2 μL | 2.5 units |
| ddH$_2$O | 13.2 μL | — |
| Total volume | 20 μL | — |

The PCR reaction is carried out according to the following procedure:

| | | |
|---|---|---|
| 94° C. | 3 min | |
| 94° C. | 30 sec | 32 cycles |
| 57° C. | 30 sec | |
| 72° C. | 45 sec | |
| 72° C. | 5 min | |

4. Preparation of Agarose Gel

The electrophoresis tank and electrophoresis comb are cleaned and air-dried, placing them on the gel maker, then preparing (as required) 80 ml of 1% gel solution. 0.8 g of agarose powder is weighted, adding 80 ml of 1×TBE buffer to mix well, and heating until transparent. 5 μL of Gold View is added when the mixture is cooled to about 60° C., pouring it into the glue maker, inserting the comb, and standing at room temperature for 40-60 min.

5. Performing Electrophoresis of PCR Products and Obtaining Detection Results

After the gel is completely solidified, taking out the PCR products, spotting the samples (two sets of PCR products) into the gel holes, and performing electrophoresis at a voltage not higher than 120 volts for about 30 min; the gel is removed after the electrophoresis. The gel block is put into a gel imaging system, taking pictures under ultraviolet light to obtain the detection results, wherein the experimental results of part of the *Ginkgo biloba* plants are shown in FIG. 1.

In FIG. 1:

Markers are: DNA Marker, Trans-Trans2K Plus II DNA Marker;

Lane 1: two bands of 1030 bp and 576 bp are obtained by amplification, indicating that the sample is a male plant;

Lane 2: two bands of 1030 bp and 576 bp are obtained by amplification, indicating that the sample is a male plant;

Lane 3: two bands of 1030 bp and 576 bp are obtained by amplification, indicating that the sample is a male plant;

Lane 4: two bands of 1030 bp and 576 bp are obtained by amplification, indicating that the sample is a male plant;

Lane 5: only one 576 bp band is obtained by amplification, indicating that the sample is a female plant;

Lane 6: only one 576 bp band is obtained by amplification, indicating that the sample is a female plant;

Lane 7: only one 576 bp band is obtained by amplification, indicating that the sample is a female plant;

Lane 8: only one 576 bp band is obtained by amplification, indicating that the sample is a female plant;

FIG. 1 only shows the detection results of some female and male plants. Through the above detection method, the collected 47 *Ginkgo biloba* plants (24 female plants and 23 male plants) are detected, and the detection results are completely consistent with the actual results, indicating that the detection method provided in this example may identify the sex of a *Ginkgo biloba* plant stably and accurately.

This application may be directly applied for identifying the sex of a *Ginkgo biloba* plant in the early stage of seedlings, thereby solving the problem that *Ginkgo biloba* seedlings cannot be accurately identified for a long time, and facilitating to optimize the allocation of male and female *Ginkgo biloba* resources and the process of rational utilization. The early gender identification of *Ginkgo biloba* seedlings makes the gender identification of *Ginkgo biloba* no longer restricted by time and space conditions, and has important use and economic value for guiding for urban greening and economic forest cultivation by utilizing *Ginkgo* biloba.

Example 2

According to the principle of sequence alignment, the Contig1634 sequence (SEQ ID NO: 5) was globally compared with the female reference genome sequence (GIGADB(doi:10.5524/100209) by BLASTN to obtain the sequence alignment results. If there is a segment with the same continuous length as Contig1634 in Female *Ginkgo biloba*, the segment will inevitably appear in the alignment results.

The results of sequence alignment show that the longest continuous same segment is only 61 bp (please see corresponding Contig1634 (928-988 nt) in FIG. 2C).

In addition, all subsequences (the number was 2042−63+1=1980) of Contig1634 sequence were obtained with a length of 63 bp and a step of 1 bp. Taking a subsequence as a query, BLASTN was used to compare it to the reference sequence. Traversal verification proved that all 63 bp subsequences (a total of 1980) in Contig1634 were aligned with the female reference genome, and there was no same alignment sequence (see Table 3 and Table 4), that is, any sequences of 63 bp or more in Contig1634 must be unique sequences of male *Ginkgo biloba*. Therefore, the same sequence as SEQ ID No: 5 sequence or its complete complementary sequence in *Ginkgo biloba* must also be a unique sequence of male *Ginkgo biloba*, and the nucleotide fragments of more than 70 bp can be used to identify male and female *Ginkgo biloba*. Furthermore, traversal verification about all 199 bp subsequences (a total of 1844) and 201 bp subsequences (a total of 1842) proved the same conclusion (see Table 3).

TABLE 3

Alignment results between reference and subsequence of 63bp, 199bp and 201bp in unique sequence of male *Ginkgo biloba* (Conting1634)

| Identity (percent) | 63bp subseq | 199bp subseq | 201bp subseq |
| --- | --- | --- | --- |
| less than 75 (excluding 75) | 0 | 0 | 0 |
| 75-95 (excluding 95) | 203 | 1226 | 1236 |
| 95-100 (excluding 100) | 176 | 64 | 64 |
| 100 | 0 | 0 | 0 |
| No hits | 1601 | 554 | 542 |
| Total | 1980 | 1844 | 1842 |

TABLE 4

| query | database | identity | align_length | mismatch | gap | query_start | query_end | target_start | target_end | evlaue | score |
| --- | --- | --- | --- | --- | --- | --- | --- | --- | --- | --- | --- |
| 887 | Reference | 100 | 61 | 0 | 0 | 3 | 63 | 2351683 | 2351743 | 1.96E−23 | 113 |
| 888 | Reference | 100 | 61 | 0 | 0 | 2 | 62 | 2351683 | 2351743 | 1.96E−23 | 113 |
| 889 | Reference | 100 | 61 | 0 | 0 | 1 | 61 | 2351683 | 2351743 | 1.96E−23 | 113 |
| 627 | Reference | 98.413 | 63 | 1 | 0 | 1 | 63 | 2351382 | 2351444 | 7.03E−23 | 111 |
| 628 | Reference | 98.413 | 63 | 1 | 0 | 1 | 63 | 2351383 | 2351445 | 7.03E−23 | 111 |
| 629 | Reference | 98.413 | 63 | 1 | 0 | 1 | 63 | 2351384 | 2351446 | 7.03E−23 | 111 |
| 630 | Reference | 98.413 | 63 | 1 | 0 | 1 | 63 | 2351385 | 2351447 | 7.03E−23 | 111 |
| 631 | Reference | 98.413 | 63 | 1 | 0 | 1 | 63 | 2351386 | 2351448 | 7.03E−23 | 111 |
| 872 | Reference | 98.413 | 63 | 1 | 0 | 1 | 63 | 2351666 | 2351728 | 7.03E−23 | 111 |
| 873 | Reference | 98.413 | 63 | 1 | 0 | 1 | 63 | 2351667 | 2351729 | 7.03E−23 | 111 |
| 874 | Reference | 98.413 | 63 | 1 | 0 | 1 | 63 | 2351668 | 2351730 | 7.03E−23 | 111 |
| 875 | Reference | 98.413 | 63 | 1 | 0 | 1 | 63 | 2351669 | 2351731 | 7.03E−23 | 111 |
| 876 | Reference | 98.413 | 63 | 1 | 0 | 1 | 63 | 2351670 | 2351732 | 7.03E−23 | 111 |
| 877 | Reference | 98.413 | 63 | 1 | 0 | 1 | 63 | 2351671 | 2351733 | 7.03E−23 | 111 |
| 878 | Reference | 98.413 | 63 | 1 | 0 | 1 | 63 | 2351672 | 2351734 | 7.03E−23 | 111 |
| 879 | Reference | 98.413 | 63 | 1 | 0 | 1 | 63 | 2351673 | 2351735 | 7.03E−23 | 111 |
| 880 | Reference | 98.413 | 63 | 1 | 0 | 1 | 63 | 2351674 | 2351736 | 7.03E−23 | 111 |
| 881 | Reference | 98.413 | 63 | 1 | 0 | 1 | 63 | 2351675 | 2351737 | 7.03E−23 | 111 |
| 882 | Reference | 98.413 | 63 | 1 | 0 | 1 | 63 | 2351676 | 2351738 | 7.03E−23 | 111 |
| 883 | Reference | 98.413 | 63 | 1 | 0 | 1 | 63 | 2351677 | 2351739 | 7.03E−23 | 111 |
| 884 | Reference | 98.413 | 63 | 1 | 0 | 1 | 63 | 2351678 | 2351740 | 7.03E−23 | 111 |
| 885 | Reference | 98.413 | 63 | 1 | 0 | 1 | 63 | 2351679 | 2351741 | 7.03E−23 | 111 |
| 886 | Reference | 98.413 | 63 | 1 | 0 | 1 | 63 | 2351680 | 2351742 | 7.03E−23 | 111 |
| 891 | Reference | 98.413 | 63 | 1 | 0 | 1 | 63 | 2351685 | 2351747 | 7.03E−23 | 111 |
| 892 | Reference | 98.413 | 63 | 1 | 0 | 1 | 63 | 2351686 | 2351748 | 7.03E−23 | 111 |
| 893 | Reference | 98.413 | 63 | 1 | 0 | 1 | 63 | 2351687 | 2351749 | 7.03E−23 | 111 |
| 894 | Reference | 98.413 | 63 | 1 | 0 | 1 | 63 | 2351688 | 2351750 | 7.03E−23 | 111 |
| 895 | Reference | 98.413 | 63 | 1 | 0 | 1 | 63 | 2351689 | 2351751 | 7.03E−23 | 111 |
| 896 | Reference | 98.413 | 63 | 1 | 0 | 1 | 63 | 2351690 | 2351752 | 7.03E−23 | 111 |
| 897 | Reference | 98.413 | 63 | 1 | 0 | 1 | 63 | 2351691 | 2351753 | 7.03E−23 | 111 |
| 898 | Reference | 98.413 | 63 | 1 | 0 | 1 | 63 | 2351692 | 2351754 | 7.03E−23 | 111 |
| 899 | Reference | 98.413 | 63 | 1 | 0 | 1 | 63 | 2351693 | 2351755 | 7.03E−23 | 111 |
| 890 | Reference | 100 | 60 | 0 | 0 | 1 | 60 | 2351684 | 2351743 | 7.03E−23 | 111 |
| 626 | Reference | 98.387 | 62 | 1 | 0 | 2 | 63 | 2351382 | 2351443 | 2.53E−22 | 110 |
| 632 | Reference | 98.387 | 62 | 1 | 0 | 1 | 62 | 2351387 | 2351448 | 2.53E−22 | 110 |
| 871 | Reference | 98.387 | 62 | 1 | 0 | 2 | 63 | 2351666 | 2351727 | 2.53E−22 | 110 |
| 900 | Reference | 98.387 | 62 | 1 | 0 | 1 | 62 | 2351694 | 2351755 | 2.53E−22 | 110 |
| 1399 | Reference | 98.361 | 61 | 1 | 0 | 3 | 63 | 2352195 | 2352255 | 9.10E−22 | 108 |
| 1400 | Reference | 98.361 | 61 | 1 | 0 | 2 | 62 | 2352195 | 2352255 | 9.10E−22 | 108 |
| 1401 | Reference | 98.361 | 61 | 1 | 0 | 1 | 61 | 2352195 | 2352255 | 9.10E−22 | 108 |
| 625 | Reference | 98.361 | 61 | 1 | 0 | 3 | 63 | 2351382 | 2351442 | 9.10E−22 | 108 |
| 633 | Reference | 98.361 | 61 | 1 | 0 | 1 | 61 | 2351388 | 2351448 | 9.10E−22 | 108 |
| 870 | Reference | 98.361 | 61 | 1 | 0 | 3 | 63 | 2351666 | 2351726 | 9.10E−22 | 108 |
| 901 | Reference | 98.361 | 61 | 1 | 0 | 1 | 61 | 2351695 | 2351755 | 9.10E−22 | 108 |
| 620 | Reference | 96.825 | 63 | 2 | 0 | 1 | 63 | 2351375 | 2351437 | 3.27E−21 | 106 |
| 621 | Reference | 96.825 | 63 | 2 | 0 | 1 | 63 | 2351376 | 2351438 | 3.27E−21 | 106 |
| 622 | Reference | 96.825 | 63 | 2 | 0 | 1 | 63 | 2351377 | 2351439 | 3.27E−21 | 106 |
| 623 | Reference | 96.825 | 63 | 2 | 0 | 1 | 63 | 2351378 | 2351440 | 3.27E−21 | 106 |
| 624 | Reference | 96.825 | 63 | 2 | 0 | 1 | 63 | 2351379 | 2351441 | 3.27E−21 | 106 |
| 833 | Reference | 96.825 | 63 | 2 | 0 | 1 | 63 | 2351627 | 2351689 | 3.27E−21 | 106 |
| 834 | Reference | 96.825 | 63 | 2 | 0 | 1 | 63 | 2351628 | 2351690 | 3.27E−21 | 106 |
| 835 | Reference | 96.825 | 63 | 2 | 0 | 1 | 63 | 2351629 | 2351691 | 3.27E−21 | 106 |
| 836 | Reference | 96.825 | 63 | 2 | 0 | 1 | 63 | 2351630 | 2351692 | 3.27E−21 | 106 |

TABLE 4-continued

| query | database | identity | align_length | mismatch | gap | query_start | query_end | target_start | target_end | evlaue | score |
|---|---|---|---|---|---|---|---|---|---|---|---|
| 837 | Reference | 96.825 | 63 | 2 | 0 | 1 | 63 | 2351631 | 2351693 | 3.27E-21 | 106 |
| 838 | Reference | 96.825 | 63 | 2 | 0 | 1 | 63 | 2351632 | 2351694 | 3.27E-21 | 106 |
| 839 | Reference | 96.825 | 63 | 2 | 0 | 1 | 63 | 2351633 | 2351695 | 3.27E-21 | 106 |
| 840 | Reference | 96.825 | 63 | 2 | 0 | 1 | 63 | 2351634 | 2351696 | 3.27E-21 | 106 |
| 841 | Reference | 96.825 | 63 | 2 | 0 | 1 | 63 | 2351635 | 2351697 | 3.27E-21 | 106 |
| 842 | Reference | 96.825 | 63 | 2 | 0 | 1 | 63 | 2351636 | 2351698 | 3.27E-21 | 106 |
| 843 | Reference | 96.825 | 63 | 2 | 0 | 1 | 63 | 2351637 | 2351699 | 3.27E-21 | 106 |
| 854 | Reference | 96.825 | 63 | 2 | 0 | 1 | 63 | 2351648 | 2351710 | 3.27E-21 | 106 |
| 855 | Reference | 96.825 | 63 | 2 | 0 | 1 | 63 | 2351649 | 2351711 | 3.27E-21 | 106 |
| 856 | Reference | 96.825 | 63 | 2 | 0 | 1 | 63 | 2351650 | 2351712 | 3.27E-21 | 106 |
| 857 | Reference | 96.825 | 63 | 2 | 0 | 1 | 63 | 2351651 | 2351713 | 3.27E-21 | 106 |
| 858 | Reference | 96.825 | 63 | 2 | 0 | 1 | 63 | 2351652 | 2351714 | 3.27E-21 | 106 |
| 859 | Reference | 96.825 | 63 | 2 | 0 | 1 | 63 | 2351653 | 2351715 | 3.27E-21 | 106 |
| 860 | Reference | 96.825 | 63 | 2 | 0 | 1 | 63 | 2351654 | 2351716 | 3.27E-21 | 106 |
| 861 | Reference | 96.825 | 63 | 2 | 0 | 1 | 63 | 2351655 | 2351717 | 3.27E-21 | 106 |
| 862 | Reference | 96.825 | 63 | 2 | 0 | 1 | 63 | 2351656 | 2351718 | 3.27E-21 | 106 |
| 863 | Reference | 96.825 | 63 | 2 | 0 | 1 | 63 | 2351657 | 2351719 | 3.27E-21 | 106 |
| 864 | Reference | 96.825 | 63 | 2 | 0 | 1 | 63 | 2351658 | 2351720 | 3.27E-21 | 106 |
| 865 | Reference | 96.825 | 63 | 2 | 0 | 1 | 63 | 2351659 | 2351721 | 3.27E-21 | 106 |
| 866 | Reference | 96.825 | 63 | 2 | 0 | 1 | 63 | 2351660 | 2351722 | 3.27E-21 | 106 |
| 867 | Reference | 96.825 | 63 | 2 | 0 | 1 | 63 | 2351661 | 2351723 | 3.27E-21 | 106 |
| 868 | Reference | 96.825 | 63 | 2 | 0 | 1 | 63 | 2351662 | 2351724 | 3.27E-21 | 106 |
| 869 | Reference | 96.825 | 63 | 2 | 0 | 1 | 63 | 2351663 | 2351725 | 3.27E-21 | 106 |
| 903 | Reference | 96.825 | 63 | 2 | 0 | 1 | 63 | 2351697 | 2351759 | 3.27E-21 | 106 |
| 904 | Reference | 96.825 | 63 | 2 | 0 | 1 | 63 | 2351698 | 2351760 | 3.27E-21 | 106 |
| 905 | Reference | 96.825 | 63 | 2 | 0 | 1 | 63 | 2351699 | 2351761 | 3.27E-21 | 106 |
| 906 | Reference | 96.825 | 63 | 2 | 0 | 1 | 63 | 2351700 | 2351762 | 3.27E-21 | 106 |
| 907 | Reference | 96.825 | 63 | 2 | 0 | 1 | 63 | 2351701 | 2351763 | 3.27E-21 | 106 |
| 908 | Reference | 96.825 | 63 | 2 | 0 | 1 | 63 | 2351702 | 2351764 | 3.27E-21 | 106 |
| 909 | Reference | 96.825 | 63 | 2 | 0 | 1 | 63 | 2351703 | 2351765 | 3.27E-21 | 106 |
| 910 | Reference | 96.825 | 63 | 2 | 0 | 1 | 63 | 2351704 | 2351766 | 3.27E-21 | 106 |
| 911 | Reference | 96.825 | 63 | 2 | 0 | 1 | 63 | 2351705 | 2351767 | 3.27E-21 | 106 |
| 912 | Reference | 96.825 | 63 | 2 | 0 | 1 | 63 | 2351706 | 2351768 | 3.27E-21 | 106 |
| 913 | Reference | 96.825 | 63 | 2 | 0 | 1 | 63 | 2351707 | 2351769 | 3.27E-21 | 106 |
| 1398 | Reference | 98.333 | 60 | 1 | 0 | 4 | 63 | 2352195 | 2352254 | 3.27E-21 | 106 |
| 1402 | Reference | 98.333 | 60 | 1 | 0 | 1 | 60 | 2352196 | 2352255 | 3.27E-21 | 106 |
| 634 | Reference | 98.333 | 60 | 1 | 0 | 1 | 60 | 2351389 | 2351448 | 3.27E-21 | 106 |
| 902 | Reference | 98.333 | 60 | 1 | 0 | 1 | 60 | 2351696 | 2351755 | 3.27E-21 | 106 |
| 832 | Reference | 96.774 | 62 | 2 | 0 | 2 | 63 | 2351627 | 2351688 | 1.18E-20 | 104 |
| 914 | Reference | 96.774 | 62 | 2 | 0 | 1 | 62 | 2351708 | 2351769 | 1.18E-20 | 104 |
| 1397 | Reference | 98.305 | 59 | 1 | 0 | 5 | 63 | 2352195 | 2352253 | 1.18E-20 | 104 |
| 1403 | Reference | 98.305 | 59 | 1 | 0 | 1 | 59 | 2352197 | 2352255 | 1.18E-20 | 104 |
| 635 | Reference | 98.305 | 59 | 1 | 0 | 1 | 59 | 2351390 | 2351448 | 1.18E-20 | 104 |
| 825 | Reference | 96.721 | 61 | 2 | 0 | 3 | 63 | 2351621 | 2351681 | 4.23E-20 | 102 |
| 826 | Reference | 96.721 | 61 | 2 | 0 | 2 | 62 | 2351621 | 2351681 | 4.23E-20 | 102 |
| 827 | Reference | 96.721 | 61 | 2 | 0 | 1 | 61 | 2351621 | 2351681 | 4.23E-20 | 102 |
| 831 | Reference | 96.721 | 61 | 2 | 0 | 3 | 63 | 2351627 | 2351687 | 4.23E-20 | 102 |
| 915 | Reference | 96.721 | 61 | 2 | 0 | 1 | 61 | 2351709 | 2351769 | 4.23E-20 | 102 |
| 1396 | Reference | 98.276 | 58 | 1 | 0 | 6 | 63 | 2352195 | 2352252 | 4.23E-20 | 102 |
| 1404 | Reference | 98.276 | 58 | 1 | 0 | 1 | 58 | 2352198 | 2352255 | 4.23E-20 | 102 |
| 636 | Reference | 98.276 | 58 | 1 | 0 | 1 | 58 | 2351391 | 2351448 | 4.23E-20 | 102 |
| 1386 | Reference | 95.238 | 63 | 3 | 0 | 1 | 63 | 2352180 | 2352242 | 1.52E-19 | 100 |
| 1387 | Reference | 95.238 | 63 | 3 | 0 | 1 | 63 | 2352181 | 2352243 | 1.52E-19 | 100 |
| 1388 | Reference | 95.238 | 63 | 3 | 0 | 1 | 63 | 2352182 | 2352244 | 1.52E-19 | 100 |
| 1389 | Reference | 95.238 | 63 | 3 | 0 | 1 | 63 | 2352183 | 2352245 | 1.52E-19 | 100 |
| 1390 | Reference | 95.238 | 63 | 3 | 0 | 1 | 63 | 2352184 | 2352246 | 1.52E-19 | 100 |
| 1391 | Reference | 95.238 | 63 | 3 | 0 | 1 | 63 | 2352185 | 2352247 | 1.52E-19 | 100 |
| 1392 | Reference | 95.238 | 63 | 3 | 0 | 1 | 63 | 2352186 | 2352248 | 1.52E-19 | 100 |
| 1393 | Reference | 95.238 | 63 | 3 | 0 | 1 | 63 | 2352187 | 2352249 | 1.52E-19 | 100 |
| 1394 | Reference | 95.238 | 63 | 3 | 0 | 1 | 63 | 2352188 | 2352250 | 1.52E-19 | 100 |
| 1395 | Reference | 95.238 | 63 | 3 | 0 | 1 | 63 | 2352189 | 2352251 | 1.52E-19 | 100 |
| 638 | Reference | 95.238 | 63 | 3 | 0 | 1 | 63 | 2351393 | 2351455 | 1.52E-19 | 100 |
| 639 | Reference | 95.238 | 63 | 3 | 0 | 1 | 63 | 2351394 | 2351456 | 1.52E-19 | 100 |
| 640 | Reference | 95.238 | 63 | 3 | 0 | 1 | 63 | 2351395 | 2351457 | 1.52E-19 | 100 |
| 829 | Reference | 95.238 | 63 | 3 | 0 | 1 | 63 | 2351623 | 2351685 | 1.52E-19 | 100 |
| 830 | Reference | 95.238 | 63 | 3 | 0 | 1 | 63 | 2351624 | 2351686 | 1.52E-19 | 100 |
| 917 | Reference | 95.238 | 63 | 3 | 0 | 1 | 63 | 2351711 | 2351773 | 1.52E-19 | 100 |
| 918 | Reference | 95.238 | 63 | 3 | 0 | 1 | 63 | 2351712 | 2351774 | 1.52E-19 | 100 |
| 919 | Reference | 95.238 | 63 | 3 | 0 | 1 | 63 | 2351713 | 2351775 | 1.52E-19 | 100 |
| 920 | Reference | 95.238 | 63 | 3 | 0 | 1 | 63 | 2351714 | 2351776 | 1.52E-19 | 100 |
| 921 | Reference | 95.238 | 63 | 3 | 0 | 1 | 63 | 2351715 | 2351777 | 1.52E-19 | 100 |
| 922 | Reference | 95.238 | 63 | 3 | 0 | 1 | 63 | 2351716 | 2351778 | 1.52E-19 | 100 |
| 1405 | Reference | 95.312 | 64 | 2 | 1 | 1 | 63 | 2352199 | 2352262 | 1.52E-19 | 100 |
| 824 | Reference | 96.667 | 60 | 2 | 0 | 4 | 63 | 2351621 | 2351680 | 1.52E-19 | 100 |
| 828 | Reference | 96.667 | 60 | 2 | 0 | 1 | 60 | 2351622 | 2351681 | 1.52E-19 | 100 |
| 916 | Reference | 96.667 | 60 | 2 | 0 | 1 | 60 | 2351710 | 2351769 | 1.52E-19 | 100 |
| 637 | Reference | 98.246 | 57 | 1 | 0 | 1 | 57 | 2351392 | 2351448 | 1.52E-19 | 100 |
| 1004 | Reference | 95.161 | 62 | 3 | 0 | 2 | 63 | 2351799 | 2351860 | 5.48E-19 | 99 |

TABLE 4-continued

| query | database | identity | align_length | mismatch | gap | query_start | query_end | target_start | target_end | evlaue | score |
|---|---|---|---|---|---|---|---|---|---|---|---|
| 1005 | Reference | 95.161 | 62 | 3 | 0 | 1 | 62 | 2351799 | 2351860 | 5.48E-19 | 99 |
| 1385 | Reference | 95.161 | 62 | 3 | 0 | 2 | 63 | 2352180 | 2352241 | 5.48E-19 | 99 |
| 641 | Reference | 95.161 | 62 | 3 | 0 | 1 | 62 | 2351396 | 2351457 | 5.48E-19 | 99 |
| 1406 | Reference | 95.238 | 63 | 2 | 1 | 1 | 62 | 2352200 | 2352262 | 5.48E-19 | 99 |
| 823 | Reference | 96.61 | 59 | 2 | 0 | 5 | 63 | 2351621 | 2351679 | 5.48E-19 | 99 |
| 1408 | Reference | 93.846 | 65 | 2 | 2 | 1 | 63 | 2352202 | 2352266 | 1.97E-18 | 97.1 |
| 1409 | Reference | 93.846 | 65 | 2 | 2 | 1 | 63 | 2352203 | 2352267 | 1.97E-18 | 97.1 |
| 1410 | Reference | 93.846 | 65 | 2 | 2 | 1 | 63 | 2352204 | 2352268 | 1.97E-18 | 97.1 |
| 1003 | Reference | 95.082 | 61 | 3 | 0 | 3 | 63 | 2351799 | 2351859 | 1.97E-18 | 97.1 |
| 1006 | Reference | 95.082 | 61 | 3 | 0 | 1 | 61 | 2351800 | 2351860 | 1.97E-18 | 97.1 |
| 1384 | Reference | 95.082 | 61 | 3 | 0 | 3 | 63 | 2352180 | 2352240 | 1.97E-18 | 97.1 |
| 642 | Reference | 95.082 | 61 | 3 | 0 | 1 | 61 | 2351397 | 2351457 | 1.97E-18 | 97.1 |
| 1407 | Reference | 95.161 | 62 | 2 | 1 | 1 | 61 | 2352201 | 2352262 | 1.97E-18 | 97.1 |
| 1007 | Reference | 96.552 | 58 | 2 | 0 | 3 | 60 | 2351803 | 2351860 | 1.97E-18 | 97.1 |
| 1008 | Reference | 96.552 | 58 | 2 | 0 | 2 | 59 | 2351803 | 2351860 | 1.97E-18 | 97.1 |
| 1009 | Reference | 96.552 | 58 | 2 | 0 | 1 | 58 | 2351803 | 2351860 | 1.97E-18 | 97.1 |
| 822 | Reference | 96.552 | 58 | 2 | 0 | 6 | 63 | 2351621 | 2351678 | 1.97E-18 | 97.1 |
| 1011 | Reference | 93.651 | 63 | 4 | 0 | 1 | 63 | 2351805 | 2351867 | 7.08E-18 | 95.3 |
| 1012 | Reference | 93.651 | 63 | 4 | 0 | 1 | 63 | 2351806 | 2351868 | 7.08E-18 | 95.3 |
| 1380 | Reference | 93.651 | 63 | 4 | 0 | 1 | 63 | 2352174 | 2352236 | 7.08E-18 | 95.3 |
| 1381 | Reference | 93.651 | 63 | 4 | 0 | 1 | 63 | 2352175 | 2352237 | 7.08E-18 | 95.3 |
| 1382 | Reference | 93.651 | 63 | 4 | 0 | 1 | 63 | 2352176 | 2352238 | 7.08E-18 | 95.3 |
| 1383 | Reference | 93.651 | 63 | 4 | 0 | 1 | 63 | 2352177 | 2352239 | 7.08E-18 | 95.3 |
| 548 | Reference | 93.651 | 63 | 4 | 0 | 1 | 63 | 2351303 | 2351365 | 7.08E-18 | 95.3 |
| 655 | Reference | 93.651 | 63 | 4 | 0 | 1 | 63 | 2351410 | 2351472 | 7.08E-18 | 95.3 |
| 656 | Reference | 93.651 | 63 | 4 | 0 | 1 | 63 | 2351411 | 2351473 | 7.08E-18 | 95.3 |
| 657 | Reference | 93.651 | 63 | 4 | 0 | 1 | 63 | 2351412 | 2351474 | 7.08E-18 | 95.3 |
| 658 | Reference | 93.651 | 63 | 4 | 0 | 1 | 63 | 2351413 | 2351475 | 7.08E-18 | 95.3 |
| 659 | Reference | 93.651 | 63 | 4 | 0 | 1 | 63 | 2351414 | 2351476 | 7.08E-18 | 95.3 |
| 660 | Reference | 93.651 | 63 | 4 | 0 | 1 | 63 | 2351415 | 2351477 | 7.08E-18 | 95.3 |
| 661 | Reference | 93.651 | 63 | 4 | 0 | 1 | 63 | 2351416 | 2351478 | 7.08E-18 | 95.3 |
| 662 | Reference | 93.651 | 63 | 4 | 0 | 1 | 63 | 2351417 | 2351479 | 7.08E-18 | 95.3 |
| 663 | Reference | 93.651 | 63 | 4 | 0 | 1 | 63 | 2351418 | 2351480 | 7.08E-18 | 95.3 |
| 664 | Reference | 93.651 | 63 | 4 | 0 | 1 | 63 | 2351419 | 2351481 | 7.08E-18 | 95.3 |
| 665 | Reference | 93.651 | 63 | 4 | 0 | 1 | 63 | 2351420 | 2351482 | 7.08E-18 | 95.3 |
| 666 | Reference | 93.651 | 63 | 4 | 0 | 1 | 63 | 2351421 | 2351483 | 7.08E-18 | 95.3 |
| 903 | Reference | 93.651 | 63 | 4 | 0 | 1 | 63 | 1673971 | 1674033 | 7.08E-18 | 95.3 |
| 904 | Reference | 93.651 | 63 | 4 | 0 | 1 | 63 | 1673972 | 1674034 | 7.08E-18 | 95.3 |
| 905 | Reference | 93.651 | 63 | 4 | 0 | 1 | 63 | 1673973 | 1674035 | 7.08E-18 | 95.3 |
| 906 | Reference | 93.651 | 63 | 4 | 0 | 1 | 63 | 1673974 | 1674036 | 7.08E-18 | 95.3 |
| 907 | Reference | 93.651 | 63 | 4 | 0 | 1 | 63 | 1673975 | 1674037 | 7.08E-18 | 95.3 |
| 908 | Reference | 93.651 | 63 | 4 | 0 | 1 | 63 | 1673976 | 1674038 | 7.08E-18 | 95.3 |
| 909 | Reference | 93.651 | 63 | 4 | 0 | 1 | 63 | 1673977 | 1674039 | 7.08E-18 | 95.3 |
| 910 | Reference | 93.651 | 63 | 4 | 0 | 1 | 63 | 1673978 | 1674040 | 7.08E-18 | 95.3 |
| 911 | Reference | 93.651 | 63 | 4 | 0 | 1 | 63 | 1673979 | 1674041 | 7.08E-18 | 95.3 |
| 912 | Reference | 93.651 | 63 | 4 | 0 | 1 | 63 | 1673980 | 1674042 | 7.08E-18 | 95.3 |
| 988 | Reference | 93.651 | 63 | 4 | 0 | 1 | 63 | 2351782 | 2351844 | 7.08E-18 | 95.3 |
| 989 | Reference | 93.651 | 63 | 4 | 0 | 1 | 63 | 2351783 | 2351845 | 7.08E-18 | 95.3 |
| 990 | Reference | 93.651 | 63 | 4 | 0 | 1 | 63 | 2351784 | 2351846 | 7.08E-18 | 95.3 |
| 991 | Reference | 93.651 | 63 | 4 | 0 | 1 | 63 | 2351785 | 2351847 | 7.08E-18 | 95.3 |
| 992 | Reference | 93.651 | 63 | 4 | 0 | 1 | 63 | 2351786 | 2351848 | 7.08E-18 | 95.3 |
| 993 | Reference | 93.651 | 63 | 4 | 0 | 1 | 63 | 2351787 | 2351849 | 7.08E-18 | 95.3 |
| 994 | Reference | 93.651 | 63 | 4 | 0 | 1 | 63 | 2351788 | 2351850 | 7.08E-18 | 95.3 |
| 995 | Reference | 93.651 | 63 | 4 | 0 | 1 | 63 | 2351789 | 2351851 | 7.08E-18 | 95.3 |
| 996 | Reference | 93.651 | 63 | 4 | 0 | 1 | 63 | 2351790 | 2351852 | 7.08E-18 | 95.3 |
| 997 | Reference | 93.651 | 63 | 4 | 0 | 1 | 63 | 2351791 | 2351853 | 7.08E-18 | 95.3 |
| 998 | Reference | 93.651 | 63 | 4 | 0 | 1 | 63 | 2351792 | 2351854 | 7.08E-18 | 95.3 |
| 999 | Reference | 93.651 | 63 | 4 | 0 | 1 | 63 | 2351793 | 2351855 | 7.08E-18 | 95.3 |
| 1411 | Reference | 93.75 | 64 | 2 | 2 | 1 | 62 | 2352205 | 2352268 | 7.08E-18 | 95.3 |
| 643 | Reference | 95 | 60 | 3 | 0 | 1 | 60 | 2351398 | 2351457 | 7.08E-18 | 95.3 |
| 1000 | Reference | 96.491 | 57 | 2 | 0 | 6 | 62 | 2351799 | 2351855 | 7.08E-18 | 95.3 |
| 1001 | Reference | 96.491 | 57 | 2 | 0 | 5 | 61 | 2351799 | 2351855 | 7.08E-18 | 95.3 |
| 1002 | Reference | 96.491 | 57 | 2 | 0 | 4 | 60 | 2351799 | 2351855 | 7.08E-18 | 95.3 |
| 1010 | Reference | 96.491 | 57 | 2 | 0 | 1 | 57 | 2351804 | 2351860 | 7.08E-18 | 95.3 |
| 821 | Reference | 96.491 | 57 | 2 | 0 | 7 | 63 | 2351621 | 2351677 | 7.08E-18 | 95.3 |
| 1013 | Reference | 93.548 | 62 | 4 | 0 | 1 | 62 | 2351807 | 2351868 | 2.55E-17 | 93.5 |
| 549 | Reference | 93.548 | 62 | 4 | 0 | 1 | 62 | 2351304 | 2351365 | 2.55E-17 | 93.5 |
| 654 | Reference | 93.548 | 62 | 4 | 0 | 2 | 63 | 2351410 | 2351471 | 2.55E-17 | 93.5 |
| 913 | Reference | 93.548 | 62 | 4 | 0 | 1 | 62 | 1673981 | 1674042 | 2.55E-17 | 93.5 |
| 1412 | Reference | 93.651 | 63 | 2 | 2 | 1 | 61 | 2352206 | 2352268 | 2.55E-17 | 93.5 |
| 644 | Reference | 94.915 | 59 | 3 | 0 | 1 | 59 | 2351399 | 2351457 | 2.55E-17 | 93.5 |
| 899 | Reference | 94.915 | 59 | 3 | 0 | 5 | 63 | 1673971 | 1674029 | 2.55E-17 | 93.5 |
| 900 | Reference | 94.915 | 59 | 3 | 0 | 4 | 62 | 1673971 | 1674029 | 2.55E-17 | 93.5 |
| 901 | Reference | 94.915 | 59 | 3 | 0 | 3 | 61 | 1673971 | 1674029 | 2.55E-17 | 93.5 |
| 902 | Reference | 94.915 | 59 | 3 | 0 | 2 | 60 | 1673971 | 1674029 | 2.55E-17 | 93.5 |
| 1413 | Reference | 95 | 60 | 1 | 2 | 3 | 60 | 2352209 | 2352268 | 2.55E-17 | 93.5 |
| 1414 | Reference | 95 | 60 | 1 | 2 | 2 | 59 | 2352209 | 2352268 | 2.55E-17 | 93.5 |
| 1415 | Reference | 95 | 60 | 1 | 2 | 1 | 58 | 2352209 | 2352268 | 2.55E-17 | 93.5 |

TABLE 4-continued

| query | database | identity | align_length | mismatch | gap | query_start | query_end | target_start | target_end | evlaue | score |
|---|---|---|---|---|---|---|---|---|---|---|---|
| 541 | Reference | 96.429 | 56 | 2 | 0 | 8 | 63 | 2351303 | 2351358 | 2.55E-17 | 93.5 |
| 542 | Reference | 96.429 | 56 | 2 | 0 | 7 | 62 | 2351303 | 2351358 | 2.55E-17 | 93.5 |
| 543 | Reference | 96.429 | 56 | 2 | 0 | 6 | 61 | 2351303 | 2351358 | 2.55E-17 | 93.5 |
| 544 | Reference | 96.429 | 56 | 2 | 0 | 5 | 60 | 2351303 | 2351358 | 2.55E-17 | 93.5 |
| 545 | Reference | 96.429 | 56 | 2 | 0 | 4 | 59 | 2351303 | 2351358 | 2.55E-17 | 93.5 |
| 546 | Reference | 96.429 | 56 | 2 | 0 | 3 | 58 | 2351303 | 2351358 | 2.55E-17 | 93.5 |
| 547 | Reference | 96.429 | 56 | 2 | 0 | 2 | 57 | 2351303 | 2351358 | 2.55E-17 | 93.5 |
| 820 | Reference | 96.429 | 56 | 2 | 0 | 8 | 63 | 2351621 | 2351676 | 2.55E-17 | 93.5 |
| 1014 | Reference | 93.443 | 61 | 4 | 0 | 1 | 61 | 2351808 | 2351868 | 9.16E-17 | 91.6 |
| 550 | Reference | 93.443 | 61 | 4 | 0 | 1 | 61 | 2351305 | 2351365 | 9.16E-17 | 91.6 |
| 653 | Reference | 93.443 | 61 | 4 | 0 | 3 | 63 | 2351410 | 2351470 | 9.16E-17 | 91.6 |
| 914 | Reference | 93.443 | 61 | 4 | 0 | 1 | 61 | 1673982 | 1674042 | 9.16E-17 | 91.6 |
| 645 | Reference | 94.828 | 58 | 3 | 0 | 1 | 58 | 2351400 | 2351457 | 9.16E-17 | 91.6 |
| 898 | Reference | 94.828 | 58 | 3 | 0 | 6 | 63 | 1673971 | 1674028 | 9.16E-17 | 91.6 |
| 1416 | Reference | 94.915 | 59 | 1 | 2 | 1 | 57 | 2352210 | 2352268 | 9.16E-17 | 91.6 |
| 271 | Reference | 96.364 | 55 | 2 | 0 | 9 | 63 | 2351008 | 2351062 | 9.16E-17 | 91.6 |
| 272 | Reference | 96.364 | 55 | 2 | 0 | 8 | 62 | 2351008 | 2351062 | 9.16E-17 | 91.6 |
| 273 | Reference | 96.364 | 55 | 2 | 0 | 7 | 61 | 2351008 | 2351062 | 9.16E-17 | 91.6 |
| 274 | Reference | 96.364 | 55 | 2 | 0 | 6 | 60 | 2351008 | 2351062 | 9.16E-17 | 91.6 |
| 275 | Reference | 96.364 | 55 | 2 | 0 | 5 | 59 | 2351008 | 2351062 | 9.16E-17 | 91.6 |
| 276 | Reference | 96.364 | 55 | 2 | 0 | 4 | 58 | 2351008 | 2351062 | 9.16E-17 | 91.6 |
| 277 | Reference | 96.364 | 55 | 2 | 0 | 3 | 57 | 2351008 | 2351062 | 9.16E-17 | 91.6 |
| 278 | Reference | 96.364 | 55 | 2 | 0 | 2 | 56 | 2351008 | 2351062 | 9.16E-17 | 91.6 |
| 279 | Reference | 96.364 | 55 | 2 | 0 | 1 | 55 | 2351008 | 2351062 | 9.16E-17 | 91.6 |
| 819 | Reference | 96.364 | 55 | 2 | 0 | 9 | 63 | 2351621 | 2351675 | 9.16E-17 | 91.6 |
| 537 | Reference | 98.077 | 52 | 1 | 0 | 12 | 63 | 2351303 | 2351354 | 9.16E-17 | 91.6 |
| 538 | Reference | 98.077 | 52 | 1 | 0 | 11 | 62 | 2351303 | 2351354 | 9.16E-17 | 91.6 |
| 539 | Reference | 98.077 | 52 | 1 | 0 | 10 | 61 | 2351303 | 2351354 | 9.16E-17 | 91.6 |
| 540 | Reference | 98.077 | 52 | 1 | 0 | 9 | 60 | 2351303 | 2351354 | 9.16E-17 | 91.6 |
| 552 | Reference | 92.063 | 63 | 5 | 0 | 1 | 63 | 2351307 | 2351369 | 3.30E-16 | 89.8 |
| 647 | Reference | 92.063 | 63 | 5 | 0 | 1 | 63 | 2351402 | 2351464 | 3.30E-16 | 89.8 |
| 648 | Reference | 92.063 | 63 | 5 | 0 | 1 | 63 | 2351403 | 2351465 | 3.30E-16 | 89.8 |
| 649 | Reference | 92.063 | 63 | 5 | 0 | 1 | 63 | 2351404 | 2351466 | 3.30E-16 | 89.8 |
| 650 | Reference | 92.063 | 63 | 5 | 0 | 1 | 63 | 2351405 | 2351467 | 3.30E-16 | 89.8 |
| 651 | Reference | 92.063 | 63 | 5 | 0 | 1 | 63 | 2351406 | 2351468 | 3.30E-16 | 89.8 |
| 652 | Reference | 92.063 | 63 | 5 | 0 | 1 | 63 | 2351407 | 2351469 | 3.30E-16 | 89.8 |
| 721 | Reference | 92.063 | 63 | 5 | 0 | 1 | 63 | 2351476 | 2351538 | 3.30E-16 | 89.8 |
| 722 | Reference | 92.063 | 63 | 5 | 0 | 1 | 63 | 2351477 | 2351539 | 3.30E-16 | 89.8 |
| 723 | Reference | 92.063 | 63 | 5 | 0 | 1 | 63 | 2351478 | 2351540 | 3.30E-16 | 89.8 |
| 806 | Reference | 92.063 | 63 | 5 | 0 | 1 | 63 | 2351600 | 2351662 | 3.30E-16 | 89.8 |
| 807 | Reference | 92.063 | 63 | 5 | 0 | 1 | 63 | 2351601 | 2351663 | 3.30E-16 | 89.8 |
| 808 | Reference | 92.063 | 63 | 5 | 0 | 1 | 63 | 2351602 | 2351664 | 3.30E-16 | 89.8 |
| 812 | Reference | 92.063 | 63 | 5 | 0 | 1 | 63 | 2351606 | 2351668 | 3.30E-16 | 89.8 |
| 813 | Reference | 92.063 | 63 | 5 | 0 | 1 | 63 | 2351607 | 2351669 | 3.30E-16 | 89.8 |
| 814 | Reference | 92.063 | 63 | 5 | 0 | 1 | 63 | 2351608 | 2351670 | 3.30E-16 | 89.8 |
| 815 | Reference | 92.063 | 63 | 5 | 0 | 1 | 63 | 2351609 | 2351671 | 3.30E-16 | 89.8 |
| 816 | Reference | 92.063 | 63 | 5 | 0 | 1 | 63 | 2351610 | 2351672 | 3.30E-16 | 89.8 |
| 817 | Reference | 92.063 | 63 | 5 | 0 | 1 | 63 | 2351611 | 2351673 | 3.30E-16 | 89.8 |
| 818 | Reference | 92.063 | 63 | 5 | 0 | 1 | 63 | 2351612 | 2351674 | 3.30E-16 | 89.8 |
| 919 | Reference | 92.063 | 63 | 5 | 0 | 1 | 63 | 1673987 | 1674049 | 3.30E-16 | 89.8 |
| 1015 | Reference | 93.333 | 60 | 4 | 0 | 1 | 60 | 2351809 | 2351868 | 3.30E-16 | 89.8 |
| 551 | Reference | 93.333 | 60 | 4 | 0 | 1 | 60 | 2351306 | 2351365 | 3.30E-16 | 89.8 |
| 915 | Reference | 93.333 | 60 | 4 | 0 | 1 | 60 | 1673983 | 1674042 | 3.30E-16 | 89.8 |
| 646 | Reference | 94.737 | 57 | 3 | 0 | 1 | 57 | 2351401 | 2351457 | 3.30E-16 | 89.8 |
| 897 | Reference | 94.737 | 57 | 3 | 0 | 7 | 63 | 1673971 | 1674027 | 3.30E-16 | 89.8 |
| 916 | Reference | 94.737 | 57 | 3 | 0 | 3 | 59 | 1673986 | 1674042 | 3.30E-16 | 89.8 |
| 917 | Reference | 94.737 | 57 | 3 | 0 | 2 | 58 | 1673986 | 1674042 | 3.30E-16 | 89.8 |
| 918 | Reference | 94.737 | 57 | 3 | 0 | 1 | 57 | 1673986 | 1674042 | 3.30E-16 | 89.8 |
| 1417 | Reference | 94.828 | 58 | 1 | 2 | 1 | 56 | 2352211 | 2352268 | 3.30E-16 | 89.8 |
| 270 | Reference | 96.296 | 54 | 2 | 0 | 10 | 63 | 2351008 | 2351061 | 3.30E-16 | 89.8 |
| 280 | Reference | 96.296 | 54 | 2 | 0 | 1 | 54 | 2351009 | 2351062 | 3.30E-16 | 89.8 |
| 536 | Reference | 98.039 | 51 | 1 | 0 | 13 | 63 | 2351303 | 2351353 | 3.30E-16 | 89.8 |
| 1022 | Reference | 91.935 | 62 | 5 | 0 | 2 | 63 | 2351817 | 2351878 | 1.19E-15 | 87.9 |
| 1023 | Reference | 91.935 | 62 | 5 | 0 | 1 | 62 | 2351817 | 2351878 | 1.19E-15 | 87.9 |
| 724 | Reference | 91.935 | 62 | 5 | 0 | 1 | 62 | 2351479 | 2351540 | 1.19E-15 | 87.9 |
| 805 | Reference | 91.935 | 62 | 5 | 0 | 2 | 63 | 2351600 | 2351661 | 1.19E-15 | 87.9 |
| 809 | Reference | 91.935 | 62 | 5 | 0 | 1 | 62 | 2351603 | 2351664 | 1.19E-15 | 87.9 |
| 1016 | Reference | 93.22 | 59 | 4 | 0 | 1 | 59 | 2351810 | 2351868 | 1.19E-15 | 87.9 |
| 810 | Reference | 93.22 | 59 | 4 | 0 | 3 | 61 | 2351606 | 2351664 | 1.19E-15 | 87.9 |
| 811 | Reference | 93.22 | 59 | 4 | 0 | 2 | 60 | 2351606 | 2351664 | 1.19E-15 | 87.9 |
| 896 | Reference | 94.643 | 56 | 3 | 0 | 8 | 63 | 1673971 | 1674026 | 1.19E-15 | 87.9 |
| 1418 | Reference | 94.737 | 57 | 1 | 2 | 1 | 55 | 2352212 | 2352268 | 1.19E-15 | 87.9 |
| 269 | Reference | 96.226 | 53 | 2 | 0 | 11 | 63 | 2351008 | 2351060 | 1.19E-15 | 87.9 |
| 281 | Reference | 96.226 | 53 | 2 | 0 | 1 | 53 | 2351010 | 2351062 | 1.19E-15 | 87.9 |
| 535 | Reference | 98 | 50 | 1 | 0 | 14 | 63 | 2351303 | 2351352 | 1.19E-15 | 87.9 |
| 1420 | Reference | 90.769 | 65 | 4 | 2 | 1 | 63 | 2352214 | 2352278 | 4.26E-15 | 86.1 |
| 1421 | Reference | 90.769 | 65 | 4 | 2 | 1 | 63 | 2352215 | 2352279 | 4.26E-15 | 86.1 |
| 1422 | Reference | 90.769 | 65 | 4 | 2 | 1 | 63 | 2352216 | 2352280 | 4.26E-15 | 86.1 |

TABLE 4-continued

| query | database | identity | align_length | mismatch | gap | query_start | query_end | target_start | target_end | evlaue | score |
|---|---|---|---|---|---|---|---|---|---|---|---|
| 1423 | Reference | 90.769 | 65 | 4 | 2 | 1 | 63 | 2352217 | 2352281 | 4.26E-15 | 86.1 |
| 1424 | Reference | 90.769 | 65 | 4 | 2 | 1 | 63 | 2352218 | 2352282 | 4.26E-15 | 86.1 |
| 1425 | Reference | 90.769 | 65 | 4 | 2 | 1 | 63 | 2352219 | 2352283 | 4.26E-15 | 86.1 |
| 1021 | Reference | 91.803 | 61 | 5 | 0 | 3 | 63 | 2351817 | 2351877 | 4.26E-15 | 86.1 |
| 1024 | Reference | 91.803 | 61 | 5 | 0 | 1 | 61 | 2351818 | 2351878 | 4.26E-15 | 86.1 |
| 725 | Reference | 91.803 | 61 | 5 | 0 | 1 | 61 | 2351480 | 2351540 | 4.26E-15 | 86.1 |
| 804 | Reference | 91.803 | 61 | 5 | 0 | 3 | 63 | 2351600 | 2351660 | 4.26E-15 | 86.1 |
| 1017 | Reference | 93.103 | 58 | 4 | 0 | 1 | 58 | 2351811 | 2351868 | 4.26E-15 | 86.1 |
| 895 | Reference | 94.545 | 55 | 3 | 0 | 9 | 63 | 1673971 | 1674025 | 4.26E-15 | 86.1 |
| 1419 | Reference | 94.643 | 56 | 1 | 2 | 1 | 54 | 2352213 | 2352268 | 4.26E-15 | 86.1 |
| 268 | Reference | 96.154 | 52 | 2 | 0 | 12 | 63 | 2351008 | 2351059 | 4.26E-15 | 86.1 |
| 282 | Reference | 96.154 | 52 | 2 | 0 | 1 | 52 | 2351011 | 2351062 | 4.26E-15 | 86.1 |
| 534 | Reference | 97.959 | 49 | 1 | 0 | 15 | 63 | 2351303 | 2351351 | 4.26E-15 | 86.1 |
| 1019 | Reference | 90.476 | 63 | 6 | 0 | 1 | 63 | 2351813 | 2351875 | 1.53E-14 | 84.2 |
| 1020 | Reference | 90.476 | 63 | 6 | 0 | 1 | 63 | 2351814 | 2351876 | 1.53E-14 | 84.2 |
| 1026 | Reference | 90.476 | 63 | 6 | 0 | 1 | 63 | 2351820 | 2351882 | 1.53E-14 | 84.2 |
| 1027 | Reference | 90.476 | 63 | 6 | 0 | 1 | 63 | 2351821 | 2351883 | 1.53E-14 | 84.2 |
| 1028 | Reference | 90.476 | 63 | 6 | 0 | 1 | 63 | 2351822 | 2351884 | 1.53E-14 | 84.2 |
| 1029 | Reference | 90.476 | 63 | 6 | 0 | 1 | 63 | 2351823 | 2351885 | 1.53E-14 | 84.2 |
| 1030 | Reference | 90.476 | 63 | 6 | 0 | 1 | 63 | 2351824 | 2351886 | 1.53E-14 | 84.2 |
| 1031 | Reference | 90.476 | 63 | 6 | 0 | 1 | 63 | 2351825 | 2351887 | 1.53E-14 | 84.2 |
| 1032 | Reference | 90.476 | 63 | 6 | 0 | 1 | 63 | 2351826 | 2351888 | 1.53E-14 | 84.2 |
| 1033 | Reference | 90.476 | 63 | 6 | 0 | 1 | 63 | 2351827 | 2351889 | 1.53E-14 | 84.2 |
| 1034 | Reference | 90.476 | 63 | 6 | 0 | 1 | 63 | 2351828 | 2351890 | 1.53E-14 | 84.2 |
| 259 | Reference | 90.476 | 63 | 6 | 0 | 1 | 63 | 2350988 | 2351050 | 1.53E-14 | 84.2 |
| 260 | Reference | 90.476 | 63 | 6 | 0 | 1 | 63 | 2350989 | 2351051 | 1.53E-14 | 84.2 |
| 261 | Reference | 90.476 | 63 | 6 | 0 | 1 | 63 | 2350990 | 2351052 | 1.53E-14 | 84.2 |
| 262 | Reference | 90.476 | 63 | 6 | 0 | 1 | 63 | 2350991 | 2351053 | 1.53E-14 | 84.2 |
| 263 | Reference | 90.476 | 63 | 6 | 0 | 1 | 63 | 2350992 | 2351054 | 1.53E-14 | 84.2 |
| 799 | Reference | 90.476 | 63 | 6 | 0 | 1 | 63 | 2351593 | 2351655 | 1.53E-14 | 84.2 |
| 800 | Reference | 90.476 | 63 | 6 | 0 | 1 | 63 | 2351594 | 2351656 | 1.53E-14 | 84.2 |
| 801 | Reference | 90.476 | 63 | 6 | 0 | 1 | 63 | 2351595 | 2351657 | 1.53E-14 | 84.2 |
| 802 | Reference | 90.476 | 63 | 6 | 0 | 1 | 63 | 2351596 | 2351658 | 1.53E-14 | 84.2 |
| 803 | Reference | 90.476 | 63 | 6 | 0 | 1 | 63 | 2351597 | 2351659 | 1.53E-14 | 84.2 |
| 892 | Reference | 90.476 | 63 | 6 | 0 | 1 | 63 | 1673960 | 1674022 | 1.53E-14 | 84.2 |
| 893 | Reference | 90.476 | 63 | 6 | 0 | 1 | 63 | 1673961 | 1674023 | 1.53E-14 | 84.2 |
| 894 | Reference | 90.476 | 63 | 6 | 0 | 1 | 63 | 1673962 | 1674024 | 1.53E-14 | 84.2 |
| 1426 | Reference | 90.625 | 64 | 4 | 2 | 1 | 62 | 2352220 | 2352283 | 1.53E-14 | 84.2 |
| 1025 | Reference | 91.667 | 60 | 5 | 0 | 1 | 60 | 2351819 | 2351878 | 1.53E-14 | 84.2 |
| 726 | Reference | 91.667 | 60 | 5 | 0 | 1 | 60 | 2351481 | 2351540 | 1.53E-14 | 84.2 |
| 1018 | Reference | 92.982 | 57 | 4 | 0 | 1 | 57 | 2351812 | 2351868 | 1.53E-14 | 84.2 |
| 267 | Reference | 96.078 | 51 | 2 | 0 | 13 | 63 | 2351008 | 2351058 | 1.53E-14 | 84.2 |
| 283 | Reference | 96.078 | 51 | 2 | 0 | 1 | 51 | 2351012 | 2351062 | 1.53E-14 | 84.2 |
| 533 | Reference | 97.917 | 48 | 1 | 0 | 16 | 63 | 2351303 | 2351350 | 1.53E-14 | 84.2 |
| 264 | Reference | 90.323 | 62 | 6 | 0 | 1 | 62 | 2350993 | 2351054 | 5.52E-14 | 82.4 |
| 798 | Reference | 90.323 | 62 | 6 | 0 | 2 | 63 | 2351593 | 2351654 | 5.52E-14 | 82.4 |
| 1427 | Reference | 90.476 | 63 | 4 | 2 | 1 | 61 | 2352221 | 2352283 | 5.52E-14 | 82.4 |
| 727 | Reference | 91.525 | 59 | 5 | 0 | 1 | 59 | 2351482 | 2351540 | 5.52E-14 | 82.4 |
| 888 | Reference | 91.525 | 59 | 5 | 0 | 5 | 63 | 1673960 | 1674018 | 5.52E-14 | 82.4 |
| 889 | Reference | 91.525 | 59 | 5 | 0 | 4 | 62 | 1673960 | 1674018 | 5.52E-14 | 82.4 |
| 890 | Reference | 91.525 | 59 | 5 | 0 | 3 | 61 | 1673960 | 1674018 | 5.52E-14 | 82.4 |
| 891 | Reference | 91.525 | 59 | 5 | 0 | 2 | 60 | 1673960 | 1674018 | 5.52E-14 | 82.4 |
| 284 | Reference | 96 | 50 | 2 | 0 | 1 | 50 | 2351013 | 2351062 | 5.52E-14 | 82.4 |
| 265 | Reference | 97.872 | 47 | 1 | 0 | 15 | 61 | 2351008 | 2351054 | 5.52E-14 | 82.4 |
| 266 | Reference | 97.872 | 47 | 1 | 0 | 14 | 60 | 2351008 | 2351054 | 5.52E-14 | 82.4 |
| 532 | Reference | 97.872 | 47 | 1 | 0 | 17 | 63 | 2351303 | 2351349 | 5.52E-14 | 82.4 |
| 1429 | Reference | 89.231 | 65 | 5 | 2 | 1 | 63 | 2352223 | 2352287 | 1.98E-13 | 80.5 |
| 1430 | Reference | 89.231 | 65 | 5 | 2 | 1 | 63 | 2352224 | 2352288 | 1.98E-13 | 80.5 |
| 1431 | Reference | 89.231 | 65 | 5 | 2 | 1 | 63 | 2352225 | 2352289 | 1.98E-13 | 80.5 |
| 1432 | Reference | 89.231 | 65 | 5 | 2 | 1 | 63 | 2352226 | 2352290 | 1.98E-13 | 80.5 |
| 1433 | Reference | 89.231 | 65 | 5 | 2 | 1 | 63 | 2352227 | 2352291 | 1.98E-13 | 80.5 |
| 1434 | Reference | 89.231 | 65 | 5 | 2 | 1 | 63 | 2352228 | 2352292 | 1.98E-13 | 80.5 |
| 294 | Reference | 89.231 | 65 | 5 | 2 | 1 | 63 | 2351023 | 2351087 | 1.98E-13 | 80.5 |
| 295 | Reference | 89.231 | 65 | 5 | 2 | 1 | 63 | 2351024 | 2351088 | 1.98E-13 | 80.5 |
| 1428 | Reference | 90.323 | 62 | 4 | 2 | 1 | 60 | 2352222 | 2352283 | 1.98E-13 | 80.5 |
| 728 | Reference | 91.379 | 58 | 5 | 0 | 1 | 58 | 2351483 | 2351540 | 1.98E-13 | 80.5 |
| 729 | Reference | 92.727 | 55 | 4 | 0 | 3 | 57 | 2351486 | 2351540 | 1.98E-13 | 80.5 |
| 730 | Reference | 92.727 | 55 | 4 | 0 | 2 | 56 | 2351486 | 2351540 | 1.98E-13 | 80.5 |
| 731 | Reference | 92.727 | 55 | 4 | 0 | 1 | 55 | 2351486 | 2351540 | 1.98E-13 | 80.5 |
| 884 | Reference | 92.727 | 55 | 4 | 0 | 9 | 63 | 1673960 | 1674014 | 1.98E-13 | 80.5 |
| 885 | Reference | 92.727 | 55 | 4 | 0 | 8 | 62 | 1673960 | 1674014 | 1.98E-13 | 80.5 |
| 886 | Reference | 92.727 | 55 | 4 | 0 | 7 | 61 | 1673960 | 1674014 | 1.98E-13 | 80.5 |
| 887 | Reference | 92.727 | 55 | 4 | 0 | 6 | 60 | 1673960 | 1674014 | 1.98E-13 | 80.5 |
| 285 | Reference | 95.918 | 49 | 2 | 0 | 1 | 49 | 2351014 | 2351062 | 1.98E-13 | 80.5 |
| 531 | Reference | 97.826 | 46 | 1 | 0 | 18 | 63 | 2351303 | 2351348 | 1.98E-13 | 80.5 |
| 733 | Reference | 88.889 | 63 | 7 | 0 | 1 | 63 | 2351488 | 2351550 | 7.13E-13 | 78.7 |
| 883 | Reference | 88.889 | 63 | 7 | 0 | 1 | 63 | 1673951 | 1674013 | 7.13E-13 | 78.7 |
| 293 | Reference | 89.062 | 64 | 5 | 2 | 2 | 63 | 2351023 | 2351086 | 7.13E-13 | 78.7 |

TABLE 4-continued

| query | database | identity | align_length | mismatch | gap | query_start | query_end | target_start | target_end | evlaue | score |
|---|---|---|---|---|---|---|---|---|---|---|---|
| 296 | Reference | 89.062 | 64 | 5 | 2 | 1 | 62 | 2351025 | 2351088 | 7.13E-13 | 78.7 |
| 732 | Reference | 92.593 | 54 | 4 | 0 | 1 | 54 | 2351487 | 2351540 | 7.13E-13 | 78.7 |
| 286 | Reference | 95.833 | 48 | 2 | 0 | 1 | 48 | 2351015 | 2351062 | 7.13E-13 | 78.7 |
| 530 | Reference | 97.778 | 45 | 1 | 0 | 19 | 63 | 2351303 | 2351347 | 7.13E-13 | 78.7 |
| 734 | Reference | 88.71 | 62 | 7 | 0 | 1 | 62 | 2351489 | 2351550 | 2.57E-12 | 76.8 |
| 292 | Reference | 88.889 | 63 | 5 | 2 | 3 | 63 | 2351023 | 2351085 | 2.57E-12 | 76.8 |
| 297 | Reference | 88.889 | 63 | 5 | 2 | 1 | 61 | 2351026 | 2351088 | 2.57E-12 | 76.8 |
| 287 | Reference | 95.745 | 47 | 2 | 0 | 1 | 47 | 2351016 | 2351062 | 2.57E-12 | 76.8 |
| 529 | Reference | 97.727 | 44 | 1 | 0 | 20 | 63 | 2351303 | 2351346 | 2.57E-12 | 76.8 |
| 289 | Reference | 87.692 | 65 | 6 | 2 | 1 | 63 | 2351018 | 2351082 | 9.23E-12 | 75 |
| 290 | Reference | 87.879 | 66 | 5 | 3 | 1 | 63 | 2351018 | 2351083 | 9.23E-12 | 75 |
| 291 | Reference | 87.879 | 66 | 5 | 3 | 1 | 63 | 2351019 | 2351084 | 9.23E-12 | 75 |
| 735 | Reference | 88.525 | 61 | 7 | 0 | 1 | 61 | 2351490 | 2351550 | 9.23E-12 | 75 |
| 298 | Reference | 88.71 | 62 | 5 | 2 | 1 | 60 | 2351027 | 2351088 | 9.23E-12 | 75 |
| 288 | Reference | 95.652 | 46 | 2 | 0 | 1 | 46 | 2351017 | 2351062 | 9.23E-12 | 75 |
| 528 | Reference | 97.674 | 43 | 1 | 0 | 21 | 63 | 2351303 | 2351345 | 9.23E-12 | 75 |
| 736 | Reference | 88.333 | 60 | 7 | 0 | 1 | 60 | 2351491 | 2351550 | 3.32E-11 | 73.1 |
| 527 | Reference | 97.619 | 42 | 1 | 0 | 22 | 63 | 2351303 | 2351344 | 3.32E-11 | 73.1 |
| 737 | Reference | 88.136 | 59 | 7 | 0 | 1 | 59 | 2351492 | 2351550 | 1.19E-10 | 71.3 |
| 526 | Reference | 97.561 | 41 | 1 | 0 | 23 | 63 | 2351303 | 2351343 | 1.19E-10 | 71.3 |
| 738 | Reference | 87.931 | 58 | 7 | 0 | 1 | 58 | 2351493 | 2351550 | 4.29E-10 | 69.4 |
| 525 | Reference | 97.5 | 40 | 1 | 0 | 24 | 63 | 2351303 | 2351342 | 4.29E-10 | 69.4 |
| 739 | Reference | 87.719 | 57 | 7 | 0 | 1 | 57 | 2351494 | 2351550 | 1.54E-09 | 67.6 |
| 524 | Reference | 97.436 | 39 | 1 | 0 | 25 | 63 | 2351303 | 2351341 | 1.54E-09 | 67.6 |
| 740 | Reference | 87.5 | 56 | 7 | 0 | 1 | 56 | 2351495 | 2351550 | 5.55E-09 | 65.8 |
| 523 | Reference | 97.368 | 38 | 1 | 0 | 26 | 63 | 2351303 | 2351340 | 5.55E-09 | 65.8 |
| 741 | Reference | 87.273 | 55 | 7 | 0 | 1 | 55 | 2351496 | 2351550 | 2.00E-08 | 63.9 |
| 522 | Reference | 97.297 | 37 | 1 | 0 | 27 | 63 | 2351303 | 2351339 | 2.00E-08 | 63.9 |
| 742 | Reference | 87.037 | 54 | 7 | 0 | 1 | 54 | 2351497 | 2351550 | 7.19E-08 | 62.1 |
| 521 | Reference | 97.222 | 36 | 1 | 0 | 28 | 63 | 2351303 | 2351338 | 7.19E-08 | 62.1 |
| 743 | Reference | 86.792 | 53 | 7 | 0 | 1 | 53 | 2351498 | 2351550 | 2.58E-07 | 60.2 |
| 517 | Reference | 100 | 32 | 0 | 0 | 32 | 63 | 2351303 | 2351334 | 2.58E-07 | 60.2 |
| 518 | Reference | 100 | 32 | 0 | 0 | 31 | 62 | 2351303 | 2351334 | 2.58E-07 | 60.2 |
| 519 | Reference | 100 | 32 | 0 | 0 | 30 | 61 | 2351303 | 2351334 | 2.58E-07 | 60.2 |
| 520 | Reference | 100 | 32 | 0 | 0 | 29 | 60 | 2351303 | 2351334 | 2.58E-07 | 60.2 |
| 744 | Reference | 86.538 | 52 | 7 | 0 | 1 | 52 | 2351499 | 2351550 | 9.29E-07 | 58.4 |
| 745 | Reference | 92.5 | 40 | 3 | 0 | 12 | 51 | 2351511 | 2351550 | 9.29E-07 | 58.4 |
| 746 | Reference | 92.5 | 40 | 3 | 0 | 11 | 50 | 2351511 | 2351550 | 9.29E-07 | 58.4 |
| 747 | Reference | 92.5 | 40 | 3 | 0 | 10 | 49 | 2351511 | 2351550 | 9.29E-07 | 58.4 |
| 748 | Reference | 92.5 | 40 | 3 | 0 | 9 | 48 | 2351511 | 2351550 | 9.29E-07 | 58.4 |
| 749 | Reference | 92.5 | 40 | 3 | 0 | 8 | 47 | 2351511 | 2351550 | 9.29E-07 | 58.4 |
| 750 | Reference | 92.5 | 40 | 3 | 0 | 7 | 46 | 2351511 | 2351550 | 9.29E-07 | 58.4 |
| 751 | Reference | 92.5 | 40 | 3 | 0 | 6 | 45 | 2351511 | 2351550 | 9.29E-07 | 58.4 |
| 752 | Reference | 92.5 | 40 | 3 | 0 | 5 | 44 | 2351511 | 2351550 | 9.29E-07 | 58.4 |
| 753 | Reference | 92.5 | 40 | 3 | 0 | 4 | 43 | 2351511 | 2351550 | 9.29E-07 | 58.4 |
| 754 | Reference | 92.5 | 40 | 3 | 0 | 3 | 42 | 2351511 | 2351550 | 9.29E-07 | 58.4 |
| 755 | Reference | 92.5 | 40 | 3 | 0 | 2 | 41 | 2351511 | 2351550 | 9.29E-07 | 58.4 |
| 756 | Reference | 92.5 | 40 | 3 | 0 | 1 | 40 | 2351511 | 2351550 | 9.29E-07 | 58.4 |
| 516 | Reference | 100 | 31 | 0 | 0 | 33 | 63 | 2351303 | 2351333 | 9.29E-07 | 58.4 |
| 757 | Reference | 92.308 | 39 | 3 | 0 | 1 | 39 | 2351512 | 2351550 | 3.34E-06 | 56.5 |
| 515 | Reference | 100 | 30 | 0 | 0 | 34 | 63 | 2351303 | 2351332 | 3.34E-06 | 56.5 |

Table 4 provides the alignment results of 63 bp subsequence and reference. At least one base of 63 bp subsequence does not match the reference.

The above descriptions are only preferred examples of this application, and are not intended to limit this application. Any modification, equivalent replacement, etc. made within the spirit and principle of this application shall be encompassed in the protection scope of this application.

What is claimed is:

1. Primers, wherein the primers specifically bind to a sequence of SEQ ID NO: 5 and produce a 1030 bp length PCR product; and the sequences of the primers are respectively represented by SEQ ID NO: 1 and SEQ ID NO: 2.

* * * * *